US012788831B2

(12) United States Patent
Pestell et al.

(10) Patent No.: US 12,788,831 B2
(45) Date of Patent: Nov. 10, 2026

(54) METHODS AND KITS FOR DIAGNOSING AND TREATING CANCERS

(71) Applicant: Baruch S. Blumberg Institute, Doylestown, PA (US)

(72) Inventors: Richard G. Pestell, Fort Lauderdale, FL (US); Zhiping Li, Wynnewood, PA (US); Xuanmao Jiao, Rockville, MD (US); Anthony Wayne Ashton, Ardmore, PA (US)

(73) Assignee: Baruch S. Blumberg Institute, Doylestown, PA (US)

( * ) Notice: Subject to any disclaimer, the term of this patent is extended or adjusted under 35 U.S.C. 154(b) by 751 days.

(21) Appl. No.: 18/032,743

(22) PCT Filed: Oct. 19, 2021

(86) PCT No.: PCT/US2021/055688

§ 371 (c)(1),
(2) Date: Apr. 19, 2023

(87) PCT Pub. No.: WO2022/087023

PCT Pub. Date: Apr. 28, 2022

(65) Prior Publication Data

US 2024/0000977 A1 Jan. 4, 2024

Related U.S. Application Data

(60) Provisional application No. 63/093,772, filed on Oct. 19, 2020.

(51) Int. Cl.

| | |
|---|---|
| ***A61K 49/00*** | (2006.01) |
| ***A61K 31/282*** | (2006.01) |
| ***A61K 31/337*** | (2006.01) |
| ***A61K 31/4745*** | (2006.01) |
| ***A61K 31/513*** | (2006.01) |
| ***A61K 31/519*** | (2006.01) |
| ***A61K 31/522*** | (2006.01) |
| ***A61K 31/675*** | (2006.01) |
| ***A61K 31/704*** | (2006.01) |
| ***A61K 31/7068*** | (2006.01) |
| ***A61K 33/243*** | (2019.01) |
| ***A61P 35/00*** | (2006.01) |
| ***C12Q 1/6804*** | (2018.01) |

(52) U.S. Cl.

CPC ........ *A61K 49/0058* (2013.01); *A61K 31/282* (2013.01); *A61K 31/337* (2013.01); *A61K 31/4745* (2013.01); *A61K 31/513* (2013.01); *A61K 31/519* (2013.01); *A61K 31/522* (2013.01); *A61K 31/675* (2013.01); *A61K 31/704* (2013.01); *A61K 31/7068* (2013.01); *A61K 33/243* (2019.01); *A61P 35/00* (2018.01); *C12Q 1/6804* (2013.01)

(58) Field of Classification Search

None

See application file for complete search history.

(56) References Cited

U.S. PATENT DOCUMENTS

| | | | | |
|---|---|---|---|---|
| 7,732,491 | B2 | 6/2010 | Sherman et al. | |
| 8,436,004 | B2 | 5/2013 | Bamba et al. | |
| 8,894,989 | B2 | 11/2014 | Xu et al. | |
| 9,453,836 | B2 | 9/2016 | Pestell | |
| 10,952,145 | B2 | 3/2021 | Kweon et al. | |
| 11,633,397 | B2 | 4/2023 | Pestell | |
| 2006/0240088 | A1 | 10/2006 | Lawrence et al. | |
| 2011/0092520 | A1 | 4/2011 | Furukawa et al. | |
| 2011/0135601 | A1 | 6/2011 | Bamba et al. | |
| 2012/0039805 | A1 | 2/2012 | Lisanti et al. | |
| 2013/0011411 | A1* | 1/2013 | Pestell ................ | C12Q 1/6886 514/19.3 |
| 2015/0344968 | A1 | 12/2015 | Johnson | |
| 2016/0139132 | A1 | 5/2016 | Lisanti et al. | |
| 2017/0290836 | A1 | 10/2017 | Fuchss et al. | |
| 2020/0016181 | A1 | 1/2020 | Boucher et al. | |
| 2020/0129476 | A1 | 4/2020 | Wolff-Winiski et al. | |
| 2020/0360380 | A1 | 11/2020 | Pestell et al. | |
| 2022/0162327 | A1 | 5/2022 | Kelly et al. | |
| 2023/0035491 | A1 | 2/2023 | Pestell et al. | |

(Continued)

FOREIGN PATENT DOCUMENTS

| | | | |
|---|---|---|---|
| WO | WO-2008/153207 | A1 | 12/2008 |
| WO | 2009149166 | A2 | 12/2009 |
| WO | WO-2009/151997 | A1 | 12/2009 |

(Continued)

OTHER PUBLICATIONS

Chu. "DACH1 inhibits cyclin D1 expression, cellular proliferation and tumor growth of renal cancer cells" 1-12. Journal of Hematology & Oncology. Web. Oct. 17, 2014; p. 1, Abstract; p. 2, col. 2, paragraph 1; p. 6, col. 2, paragraph 1; p. 9, col. 1, paragraph 1; DOI: 10.1186/s13045-014-0073-5, 12 pages.

Wu. "Cell Fate Factor DACH1 Represses YB-1 -mediated Oncogenic Transcription and Translation". Cancer Res. Web. Feb. 1, 2014; p. 4, paragraph 3; figure 1; DOI: 10.1158/0008-54 72.CAN-13-2466, pp. 829-839.

Watanabe. "Homozygously deleted gene DACH1 regulates tumor-initiating activity of gliomacells" 12384-12389. Proceedings of the National Academy of Sciences. Web. Jul. 26, 2011; abstract; p. 12384, col. 1, paragraph 2; DOI: 10.1073/pnas.0906930108, pp. 12384-12389.

International Search Report and Written Opinion for International PCT Application No. PCT/US2021/055688 (WO2022087023) dated Feb. 18, 2022, pp. 12.

(Continued)

*Primary Examiner* — Peter Johansen

(74) *Attorney, Agent, or Firm* — Goodwin Procter LLP

(57) ABSTRACT

Methods and/or kits for aiding, preventing, treating, or ameliorating the negative effects for a patient suffering from cancer are disclosed herein. In accordance with an aspect of the invention, that includes determining a sensitivity of one or more cancer cells by administering an immunohistochemical stain configured to determine an abundance of DACH1a gene.

13 Claims, 35 Drawing Sheets

Specification includes a Sequence Listing.

(56) References Cited

U.S. PATENT DOCUMENTS

| | | | |
|---|---|---|---|
| 2023/0364085 | A1 | 11/2023 | Pestell |
| 2024/0224960 | A1 | 7/2024 | Pestell |

FOREIGN PATENT DOCUMENTS

| | | | |
|---|---|---|---|
| WO | WO-2010/060032 | A1 | 5/2010 |
| WO | 2011085134 | A2 | 7/2011 |
| WO | WO-2016/025473 | A2 | 2/2016 |
| WO | WO-2018/178040 | A1 | 10/2018 |
| WO | 2022087023 | A1 | 4/2022 |

OTHER PUBLICATIONS

Bucher, N, and C D Britten. "G2 checkpoint abrogation and checkpoint kinase-1 targeting in the treatment of cancer." British journal of cancer vol. 98,3 (2008): 523-8.

Chen K et al., Acetylation of the cell-fate factor dachshund determines p53 binding and signaling modules in breast cancer. Oncotarget. Jun. 2013; 4(6):923-35.

Chen K et al., RG. Dachshund binds p53 to block the growth of lung adenocarcinoma cells. Cancer Res. Jun. 1, 2013;73(11):3262-74.

Chen K et al., The endogenous cell-fate factor dachshund restrains prostate epithelial cell migration via repression of cytokine secretion via a cxcl signaling module. Cancer Res. May 15, 2015;75(10):1992-2004. Epub Mar. 13, 2015.

Chen, Tao et al. "Targeting the S and G2 checkpoint to treat cancer." Drug discovery today vol. 17,5-6 (2012): 194-202.

D'Adda di Fagagna, F et al. "Functions of poly(ADP-ribose) polymerase in controlling telomere length and chromosomal stability." Nature genetics vol. 23,1 (1999): 76-80.

DeAngelis T et al., The type 1 insulin-like growth factor receptor and resistance to DACH1. Cell Cycle. Jun. 15, 2011;10(12):1956-9. Epub Jun. 15, 2011.

Doke et al., Transcriptome-wide association analysis identifies DACH1 as a kidney disease risk gene that contributes to fibrosis. J Clin Invest. May 17, 2021;131(10):e141801.

Jiao X et al., Dachshund Depletion Disrupts Mammary Gland Development and Diverts the Composition of the Mammary Gland Progenitor Pool. Stem Cell Reports. Jan. 8, 2019;12(1):135-151. Epub Dec. 13, 2018.

Kong D et al., The retinal determination gene network: from developmental regulator to cancer therapeutic target. Oncotarget. Aug. 2, 2016;7(31):50755-50765.

Liu Q et al., DACH1 antagonizes CXCL8 to repress tumorigenesis of lung adenocarcinoma and improve prognosis. J Hematol Oncol. Apr. 10, 2018;11(1):53. doi: 10.1186/s13045-018-0597-1.

Liu Q, et al., Correction: DACH1 antagonizes CXCL8 to repress tumorigenesis of lung adenocarcinoma and improve prognosis. J Hematol Oncol. Dec. 13, 2022;15(1):175. Erratum for: J Hematol Oncol. Apr. 10, 2018;11(1):53.

Nan F et al., Altered expression of DACH1 and cyclin D1 in endometrial cancer. Cancer Biol Ther. Aug. 2009; 8(16):1534-9, Epub Aug. 8, 2009.

Ozcan L et al., Hepatocyte DACH1 Is Increased in Obesity via Nuclear Exclusion of HDAC4 and Promotes Hepatic Insulin Resistance. Cell Rep. Jun. 7, 2016;15(10):2214-2225. Epub May 26, 2016.

Ozcan L et al., Correction, Hepatocyte DACH1 Is Increased in Obesity via Nuclear Exclusion of HDAC4 and Promotes Hepatic Insulin Resistance. Cell Rep. Jun. 21, 2022;39(12):111015.

Popov et al., The Dachshund gene in development and hormone-responsive tumorigenesis. Trends Endocrinol Metab. Jan. 2010; 21(1):41-9. Epub Nov. 5, 2009.

Popov VM et al., The cell fate determination factor DACH1 is expressed in estrogen receptor-alpha-positive breast cancer and represses estrogen receptor-alpha signaling. Cancer Res. Jul. 15, 2009;69(14):5752-60.

Schild R et al., Double homozygous missense mutations in DACH1 and BMP4 in a patient with bilateral cystic renal dysplasia. Nephrol Dial Transplant. Jan. 2013; 28(1):227-32 Epub Dec. 21, 2012.

Sundaram K et al., DACH1 negatively regulates the human RANK ligand gene expression in stromal/preosteoblast cells. J Cell Biochem. Apr. 15, 2008;103(6):1747-59.

Sunde et al., Expression profiling identifies altered expression of genes that contribute to the inhibition of transforming growth factor-beta signaling in ovarian cancer. Cancer Res. Sep. 1, 2006;66(17):8404-12.

Velasco-Velázquez et al., Breast cancer stem cells. Int J Biochem Cell Biol. Apr. 2012; 44(4):573-7. Epub Jan. 9, 2012.

Wu et al., Endogenous Dach1 in cancer. Oncoscience. Sep. 23, 2015;2(10):803-4.

Wu K et al., Cell fate determination factor Dachshund reprograms breast cancer stem cell function. J Biol Chem. Jan. 21, 2011;286(3):2132-42.

Wu K et al., DACH1 inhibits transforming growth factor-beta signaling through binding Smad4. J Biol Chem. Dec. 19, 2003;278(51):51673-84. Epub Oct. 2, 2003.

Wu K et al., DACH1 is a cell fate determination factor that inhibits cyclin D1 and breast tumor growth. Mol Cell Biol. Oct. 2006; 26(19):7116-29.

Wu K et al., Dachshund inhibits oncogene-induced breast cancer cellular migration and invasion through suppression of interleukin-8. Proc Natl Acad Sci U S A. May 13, 2008;105(19):6924-9. Epub May 8, 2008.

Wu K et al., The cell fate determination factor dachshund inhibits androgen receptor signaling and prostate cancer cellular growth. Cancer Res. Apr. 15, 2009;69(8):3347-55. Epub Apr. 7, 2009.

Wu K, et al., Cell fate determination factor DACH1 inhibits c-Jun-induced contact-independent growth. Mol Biol Cell. Mar. 2007; 18(3):755-67. Epub Dec. 20, 2006.

Xu H et al., DACH1 suppresses breast cancer as a negative regulator of CD44. Sci Rep. Jun. 28, 2017;7(1):4361.

Zheng Z et al., An ATF6-tPA pathway in hepatocytes contributes to systemic fibrinolysis and is repressed by DACH1. Blood. Feb. 14, 2019;133(7):743-753. Epub Dec. 1, 2018.

Zhou J et al., Attenuation of Forkhead signaling by the retinal determination factor DACH1. Proc Natl Acad Sci U S A. Apr. 13, 2010;107(15):6864-9. Epub Mar. 29, 2010.

Zhou J et al., Transcription elongation regulator 1 is a co-integrator of the cell fate determination factor Dachshund homolog 1. J Biol Chem. Dec. 17, 2010;285(51):40342-50. Epub Oct. 18, 2010.

* cited by examiner

| Non-replicating S-phase | DMSO | AZD1775 |
|---|---|---|
| Wt | 4.0% | 13.8% |
| DACH-KO | 1.9% | 38.3% |

The analysis tested 3 pairs between the 3 tracks in the OncoPrint.

☑ Mutual exclusivity ☑ Co-occurance ☐ Significant only

| A | B | Neither | A Not B | B Not A | Both | Log2 Odds Ratio | p-Value | q-Value ▲ | Tendency |
|---|---|---|---|---|---|---|---|---|---|
| DACH1 | SETD2 | 447 | 27 | 15 | 0 | <-3 | 0.421 | 0.803 | Mutual exclusivity |
| DACH1 | EPB41L4B | 455 | 27 | 7 | 0 | <-3 | 0.670 | 0.803 | Mutual exclusivity |
| SETD2 | EPB41L4B | 467 | 15 | 7 | 0 | <-3 | 0.803 | 0.803 | Mutual exclusivity |

SEQUENCE LISTING

```
<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: Synthetic

<400> SEQUENCE: 1

Pro Leu Ser Thr Pro Thr Ala Arg Asp Ser Leu Asp Lys
1               5                   10


<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Glu Arg Thr Ile Gln Asp Gly Arg Leu Tyr Leu Lys Thr Thr Val Met
1               5                   10                  15

Tyr


<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

Gly Arg Arg Pro Gly Ser His Pro Ser Ser His Arg Ser Ser
1               5                   10


<210> SEQ ID NO 4
<211> LENGTH: 14
<212> TYPE: PRT
<213> ORGANISM: Artificial Sequence
<220> FEATURE:
<223> OTHER INFORMATION: Synthetic
```

-continued

```
<400> SEQUENCE: 4

Asn Gln His Gly Ala Asp Ser Glu Asn Gly Asp Met Asn Ser
1               5                   10


<210> SEQ ID NO 5
<211> LENGTH: 16
<212> TYPE: PRT
<213> ORGANISM: Artificial Sequence
<220> FEATURE:
<223> OTHER INFORMATION: Synthetic

<400> SEQUENCE: 5

Glu Arg Val Pro Asp Pro Ser Pro Ser Pro Ala Pro Ser Leu Glu Cys
1               5                   10                  15
```

METHODS AND KITS FOR DIAGNOSING AND TREATING CANCERS

CROSS-REFERENCE TO RELATED APPLICATIONS

This application is a National Stage Application of International Patent Application No. PCT/US2021/055688, filed on Oct. 19, 2021, which claims priority to U.S. Provisional Patent Application Ser. No. 63/093,772, titled METHODS AND KITS FOR DIAGNOSING AND TREATING CANCERS, which was filed on Oct. 19, 2020, each of which are incorporated herein by reference for all purposes, in their entireties.

FEDERALLY SPONSORED RESEARCH OR DEVELOPMENT

This invention was made with government support under contract, R01 CA 132115-05A1, awarded by the National Institute of Health (NIH). The government has certain rights in the invention.

SEQUENCE LISTING

This application contains a Sequence Listing which has been submitted electronically in TXT format and is hereby incorporated by reference in its entirety. The Sequence Listing is named "EGO_001WO_Sequence_Listing", was created on Apr. 18, 2023, and is 1,447 bytes in size.

BACKGROUND

All cells possess mechanisms to maintain integrity of the cellular genome through detection and repair of, for example, adduct formation, cross-linking, single-strand breaks, and double-strand DNA breaks. The mechanisms of detection and damage repair, collectively, are called DNA repair. DNA repair functions can be performed as a result of lesions that arise from exposure to a variety of environmental chemical and physical agents, as well as from toxic agents generated intracellularly in normal cellular metabolism. Because DNA provides the information required for cell, tissue, and organism function, a large amount of cellular energy is devoted to maintaining intact structure of the genome.

The most genotoxic damages are those which induce DNA chain disruptions, particularly double-strand breaks. DNA double-strand breaks (dsbs) can be induced by chemical or physical agents, including intercalating agents, electrophilic compounds, and ionizing radiation. At least two pathways responsible for the repair of DNA dsbs exist, i.e., homologous recombination (HR) and nonhomologous end joining (NHEJ). The former reaction requires undamaged DNA from the homologous chromosome to be used as a template in the repair of the DNA discontinuity. NHEJ, in contrast, is DNA homology independent and simply requires two free DNA ends to be relegated. The exact molecular mechanisms by which both HR and NHEJ are affected remain to be elucidated.

Cell cycle checkpoints are surveillance mechanisms that monitor and coordinate the order and fidelity of cell cycle events. When defects in the division program of a cell are detected, checkpoints prevent the pursuant cell cycle transition through regulation of the relevant cyclin-cdk complexes. Checkpoints that respond to DNA damage have been described for the G1, S and G2 phases of the cell cycle. For example, the p53 tumor suppressor is a key regulator of G1/S checkpoints, and can promote cell cycle delay or apoptosis in response to DNA damage.

Cancer cells that possess a deficient G1 checkpoint, which impairs the ability of the cell to halt the cell cycle in order to repair DNA damage prior to replication, gives these cancer cells a means to accumulate mutations and propagate irregularities that are favorable to cancer formation. These cancer cells are therefore reliant on the G2 checkpoint to prevent excessive DNA damage that leads to apoptosis via mitotic catastrophe (Chen T, et al. Drug Discovery Today. 2012; 17(5-6): 194-202; Bucher N, et al., British Journal of Cancer. 2008; 98(3): 523-8). In normal cells, the G1 checkpoint is not compromised; therefore, the G2 checkpoint is not burdened with halting the cell cycle prior to DNA damage repair. Thus, modulation of the G2 checkpoint selectively impacts tumorigenesis rather than normal cell growth.

Poly ADP ribose polymerase (PARP) contributes to various DNA-related functions including cell proliferation, differentiation, apoptosis, and DNA repair, and also affects telomere length and chromosome stability (d'Adda di Fagagna et al., 1999, Nature Gen., 23 (1): 76-80). Overactivation of PARP induced by oxidative stress consumes $NAD^+$ and consequently ATP, leading to cellular dysfunction or necrosis. This cell suicide mechanism is found in cancer, stroke, myocardial ischemia, diabetes, diabetic cardiovascular dysfunction, shock, traumatic central nervous system injury, arthritis, colitis, allergic encephalomyelitis, and various other forms involved in the pathological mechanism of inflammation. PARP is associated with the function of several transcription factors and has also been demonstrated to regulate that function. Because of the diverse functions of PARP, it is a target for a variety of serious conditions, including various forms of cancer and neurodegenerative diseases.

PARP inhibitors may help certain parts of patients who have mutations in their genes. These mutations predispose patients to early-onset cancer and have been found in prostate cancer as well as in breast cancer, ovarian cancer, and pancreatic cancer.

There is an ongoing need for improved means for identifying cancers sensitive to certain pharmaceutical compounds.

SUMMARY OF THE INVENTION

Aspects of the invention provide methods of aiding a patient suffering from cancer. For instance, the methods may be useful for preventing, treating, or ameliorating the effects of cancer. Without being limited to any particular theory, the inventors surprisingly discovered that the sensitivity of various human cancers to certain pharmaceutical treatments can be determined, in part, by assessing an abundance of DACH1 in such cancer cells. For example, it was unexpected that a deletion or a presence of the DACH1a gene in cancer cell(s), such as prostate cancer, breast cancer, and/or lung cancer, can be used to determine the sensitivity of such cancer cells to specific anti-cancer pharmaceutical drugs. Further, it was discovered that the presence or deletion of DACH1 gene from prostate, lung, and breast cancer cell(s) significantly effects the survivability of human subjects having such cancers, as seen in FIGS. 1-3.

In accordance with an aspect of the invention, provided is a method for aiding a subject suffering from cancer. The method may include determining a sensitivity of one or more cancer cells by administering an immunohistochemical stain configured to determine an abundance of DACH1a gene.

In some cases, the method includes determining the sensitivity of the one or more cancer cells comprises the step of determining a reduction in the abundance of the DACH1 gene abundance in the one or more cancer cells. The method may further comprise providing a PARP inhibitor (NAD-dependent or NAD-independent), a chemotherapy from a DNA damaging agent, a TGFb inhibitor, a g irradiation (alone or in combination with a DNA-PK inhibitor), an androgen antagonist (i.e. flutamide), DNA-PK inhibitor, a WEE1 inhibitor, a prodrug thereof, a salt thereof, or a combination of two or more thereof to a subject. For example, the method may include administering a therapeutically effective amount of a composition comprising DNA-PK inhibitor, a WEE1 inhibitor, a prodrug thereof, a salt thereof, or a combination of two or more thereof or administering a composition comprising a PARP inhibitor, a prodrug thereof, a salt thereof, or a combination of two or more thereof based on the determined sensitivity of the one or more cancer cells.

The WEE1 inhibitor employed in the methods disclosed herein may be selected from AZD1775 (MK1775), 2-allyl-1-[6-(1-hydroxy-1-methylethyl)pyridin-2-yl]-6-{[4-(4-methylpiperazin-1-yl)phenyl]aminol-1,2-dihydro-3H-pyrazolo[3,4-d]pyrimidin-3-one, 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d]pyrimidin-2(1H)-one, and a combination of two or more thereof. Additionally or alternatively, the method may employ one or more DNA-PK inhibitor(s), including, e.g., AZD7648 and/or M3814.

According to another aspect of the invention, provided is a method for aiding and/or treating a human suffering from cancer. The method may include administering an immunohistochemical stain configured to couple to an expression of the DACH1 gene to a human having one or more cancer cells; determining a deletion of the DACH1 gene in the one or more cancer cells; and determining a sensitivity of the one or more cancer cells based on the determination of the deletion of the DACH1 gene from the one or more cancer cells.

In accordance with another aspect of the invention, provided is kit containing components, equipment, and/or compositions for employing the methods disclosed herein.

BRIEF DESCRIPTION OF THE DRAWINGS

The features, and advantages of the invention will be apparent from the following more detailed description of certain embodiments of the invention and as illustrated in the accompanying drawings in which.

Figure 1:
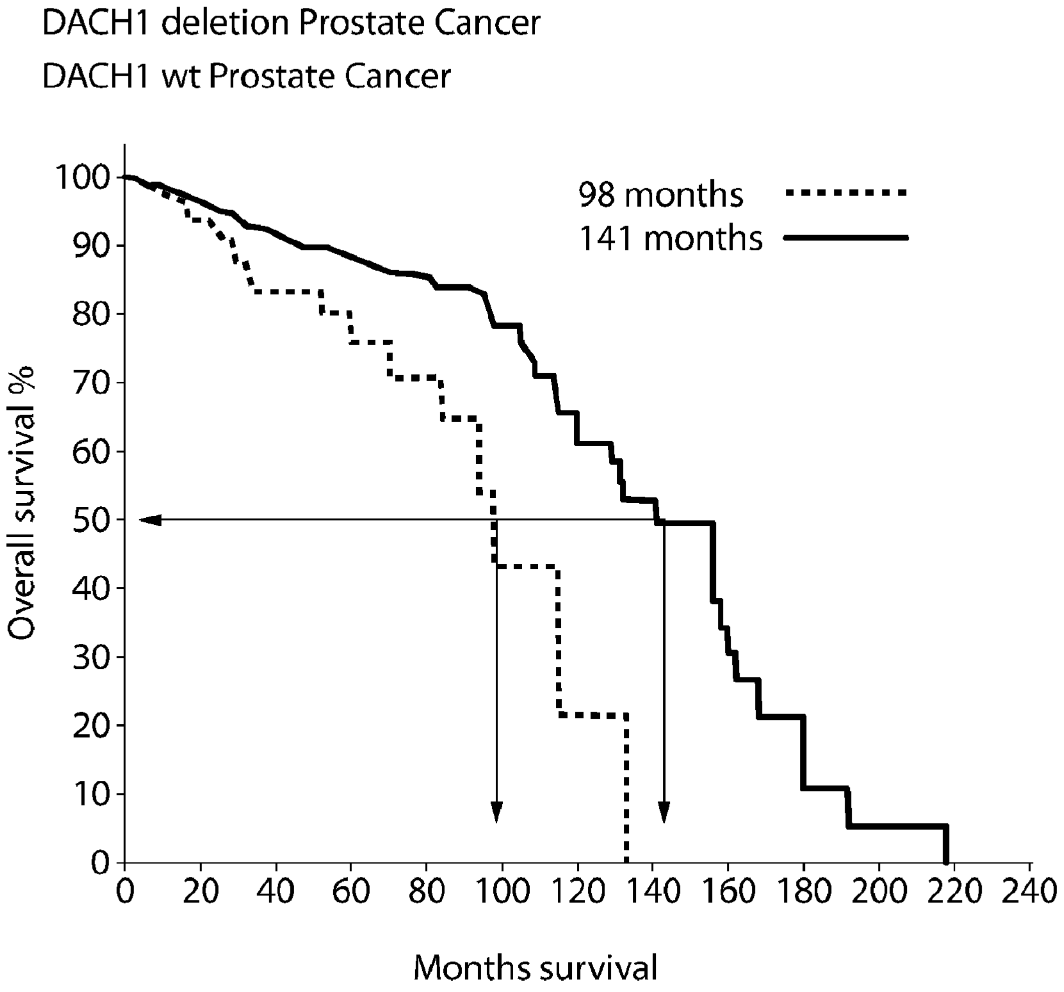
FIG. 1 is a graph showing the survivability of human subjects having prostate cancer exhibiting DACH1 deletion ($^{-/-}$) as compared to DACH1 presence ($^{+/+}$) in accordance with aspects of the invention.

It should be understood that the various aspects are not limited to the compositions, arrangements, and instrumentality shown in the figure.

DETAILED DESCRIPTION OF EMBODIMENTS OF THE INVENTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation.

As used herein and in the appended claims, the singular forms “a”, “an”, and “the” include plural references unless the context dictates otherwise. The singular form of any class of the ingredients refers not only to one chemical species within that class, but also to a mixture of those chemical species. The terms “a” (or “an”), “one or more” and “at least one” may be used interchangeably herein. The terms “comprising”, “including”, and “having” may be used interchangeably. The term “include” should be interpreted as “include, but are not limited to”. The term “including” should be interpreted as “including, but are not limited to”.

As used throughout, ranges are used as shorthand for describing each and every value that is within the range. Any value within the range can be selected as the terminus of the range. Thus, a range from 1-5, includes specifically 1, 2, 3, 4 and 5, as well as subranges such as 2-5, 3-5, 2-3, 2-4, 1-4, etc.

The term “about” when referring to a number means any number within a range of 10% of the number. For example, the phrase “about 2.0 wt. %” refers to a number between and including 1.8 wt. % and 2.2 wt. %.

All references cited herein are hereby incorporated by reference in their entireties. In the event of a conflict in a definition in the present disclosure and that of a cited reference, the present disclosure controls.

The abbreviations and symbols as used herein, unless indicated otherwise, take their ordinary meaning. The abbreviation “wt. %” means percent by weight with respect to the composition. The symbol “°” refers to a degree, such as a temperature degree or a degree of an angle. The symbols “h”, “min”, “mL”, “nm”, “μm” means hour, minute, milliliter, nanometer, and micrometer, respectively.

“Treatment” or “treating” refers to a therapeutic intervention that ameliorates a sign or symptom of a disease or pathological condition after it has begun to develop. As used herein, the term “ameliorating,” with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase “treating a disease” is inclusive of inhibiting the full development of a disease or condition, for example, in a subject who is at risk for a disease, or who has a disease, such as cancer or a disease associated with a compromised immune system. “Preventing” a disease or condition refers to prophylactically administering a composition to a subject who does not exhibit signs of a disease or exhibits only early signs of the disease, for the purpose of decreasing the risk of developing a pathology or condition, or diminishing the severity of a pathology or condition.

When referring to chemical structures, and names, the symbols “C”, “H”, and “O” mean carbon, hydrogen, and oxygen, respectively. The symbols “—”, “═” and “≡” mean single bond, double bond, and triple bond respectively.

Any member in a list of species that are used to exemplify or define a genus, may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

All components and elements positively set forth in this disclosure can be negatively excluded from the claims. In other words, the methods, kits, or compositions of the instant disclosure can be free or essentially free of all components and/or elements positively recited throughout the instant disclosure.

For readability purposes, the chemical functional groups are in their adjective form; for each of the adjective, the word "group" is assumed. For example, the adjective "alkyl" without a nouns thereafter, should be read as "an alkyl group." References to the chemical functional groups described herein are further discussed below.

Aspects of the invention provide methods of aiding a patient suffering from cancer. In some instances, the methods may be useful for preventing, treating, or ameliorating the effects of cancer. In at least one instance, the method reduces the likelihood of metastasis of a cancer in a subject. Without being limited to any particular theory, the inventors surprisingly discovered that the sensitivity of various human cancers to certain pharmaceutical treatments can be determined, in part, by assessing an abundance of DACH1 in such cancer cells. For example, it was unexpected that a deletion or a presence of the DACH1a gene in cancer cell(s), such as prostate cancer, breast cancer, and/or lung cancer, can be used to determine the sensitivity of such cancer cells to specific anti-cancer pharmaceutical drugs. Additionally, it is believed that determining an abundance or lack thereof of DACH1a gene can be used to determine the sensitivity to certain anti-cancer pharmaceutical drugs for glioblastoma multiforme cancers.

Figure 2:
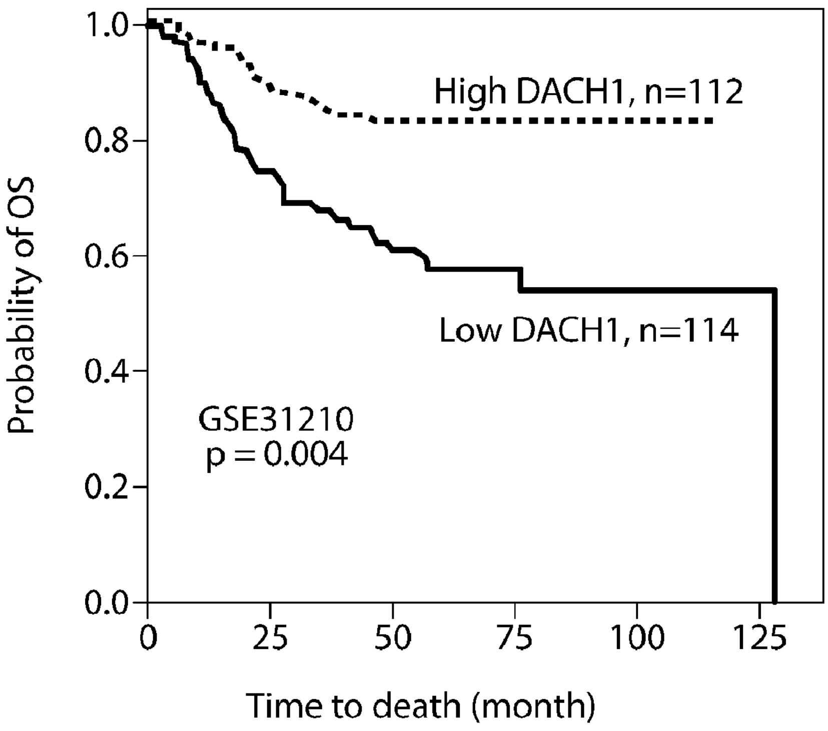
FIG. 2 is a graph showing the survivability of human subjects having lung adenocarcinoma cancer exhibiting DACH1 deletion as compared to DACH1 presence according to aspects of the invention.
Figure 3:
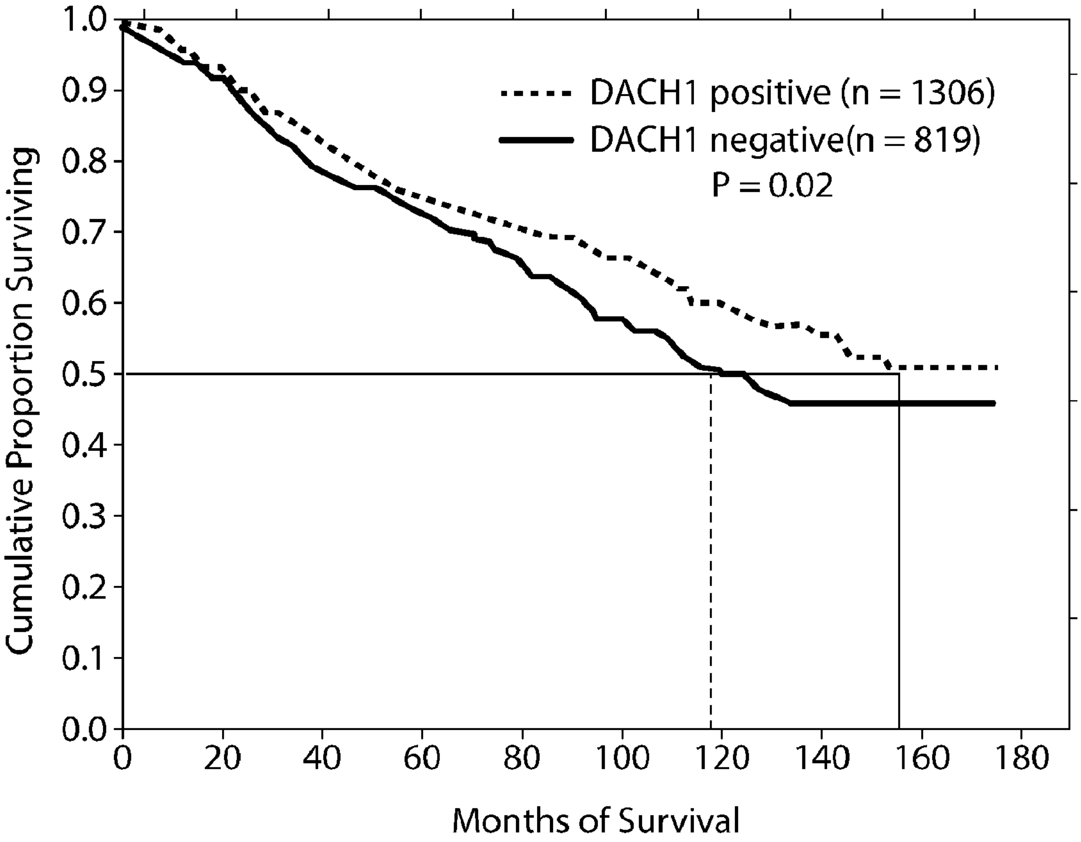
FIG. 3 is a graph showing the survivability of human subjects having breast cancer exhibiting DACH1 deletion as compared to DACH1 presence in accordance with aspects of the invention.

The DACH1 gene is used to produce proteins that participate in DNA repair. Without being limited to any specific theory, it is believed that DACH1 encodes a chromatin-associated protein that associates with other DNA-binding transcription factors to regulate gene expression, mRNA translation, coactivator binding, and cell fate determination during development. It was discovered that the presence or deletion of DACH1 gene from prostate, lung, and breast cancer cell(s) significantly effects the survivability of human subjects having such cancers, as seen in FIGS. 1-3.

In accordance with an aspect of the invention, provided is a method for aiding a subject suffering from cancer. The method typically comprises determining a sensitivity of one or more cancer cells by administering an immunohistochemical stain configured to determine an abundance of DACH1 gene. Preferably, the sensitivity of the one or more cancers is determined by assessing if the cancer cells have a deletion or a presence of the DACH1 gene.

The determination of the presence or deletion of the DACH1 gene can be based on determining an abundance of the DACH1 gene or a portion thereof, an mRNA encoding the DACH1 gene or portion thereof, and/or determining an abundance or reduction in the abundance of protein encoded on the DACH1 gene or portion thereof (such as a DACH1 protein). For example, the method may include determining if a portion comprising about 10% or more, about 20% or more, about 30% or more, about 40% or more, about 50% or more, about 60% or more, about 70% or more, about 80% or more, or 90% or more of the DACH1a gene is present in the cancerous cells. In some cases, the method may include determining if the cancer cell(s) have a deep deletion or a shallow deletion in the DACH1a gene. Generally, a deep deletion is a homozygous gene deletion, while a shallow deletion may correspond to a heterozygous deletion. In some cases, however, the method includes determining if the whole of DACH1a gene has been deleted from one or more cancer cells.

Figure 4:
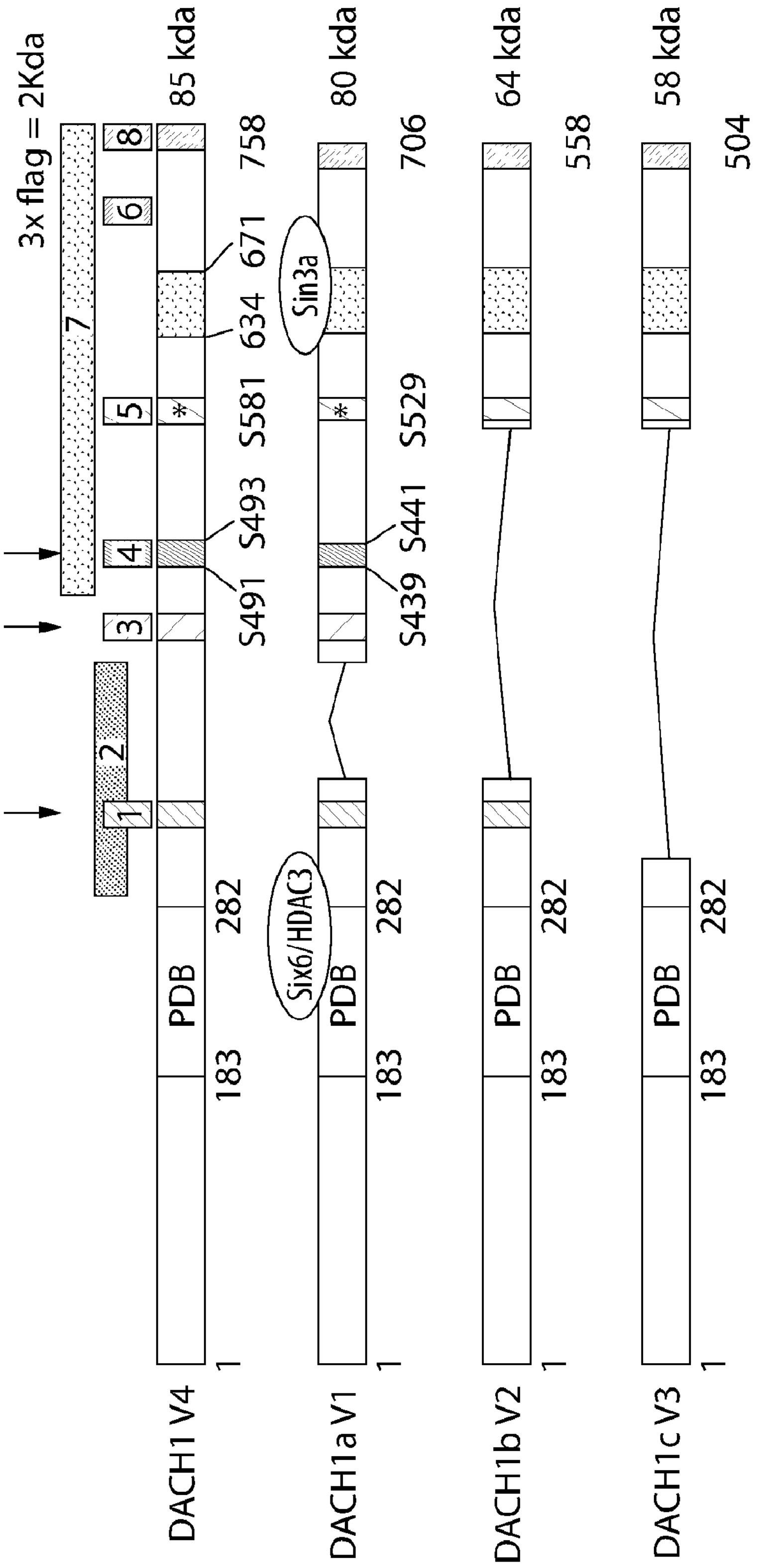
FIG. 4 shows representations of exemplary DACH1 isoform specific antibodies according to aspects of the invention.

In some embodiments, the method uses DACH1 isoform antibodies, such as (shown in FIG. 4), to determine if the DACH1 gene or a portion thereof has been deleted from the one or more cancer cell. Examples of antibody configured to target DACH1 include: abcam (ab31588 579-591 and the amino acids are PLSTPTARDSLDK); Pestell lab (742-758 and the amino acids are ERTIQDGRLYLKTTVMY); DACH1a (449-462 GRRPGSHPSSHRSS); DACH1 Pestell lab (360-373 NQHGADSENGDMNS); DACH1 Pestell lab (Ser 439 ERVPD{pS}PSPAPSLEC); Sigma ab12938 (290-432 79 kda on Western); Sigma ab12672 (290-432 79 kda nuclear IHC); DACH1 (10914-1-AP); and Novogen DACH1 AA 720-740. Regarding tissue specificity, DACH1 is widely expressed; DACH1a (Isoform 2) is expressed in brain, heart, kidney, liver, leukocytes, and spleen. DACH1b (Isoform 3) is expressed in liver and heart; and DACH1c (Isoform 4) is express in spleen. In a preferred embodiment, antibodies DACH1ab, sigma ab12938, DACH1a, DACH1ab, abcam: ab31588, and a combination of two or more thereof are used to measure an abundance of the DACH1 and/or DACH1a. The DACH1 isoform antibodies may be configured to bind to a DACH1 protein to determine the presence or deletion of the DACH1 gene in the one or more cancer cells. In at least one preferred embodiment, the DACH1 isoform antibodies may be configured to bind to the DACH1a protein or a portion thereof to determine the abundance or a reduction in the abundance of the DACH1a protein.

The immunohistochemical stains employed with the method are typically an antibody configured to target DACH1 gene, a mRNA thereof, or a DACH1 protein. The immunohistochemical stains also include a marker. The markers of the antibody for immunohistochemical stains may be nestin, β3-tubulin, vimentin, rhodopsin, Ki-67, PKC-α marker, GDNF, GATA6, GFAP or a combination of two or more thereof. Examples of antibodies that may, in some cases, be useful for determining an abundance of DACH1 include, e.g., DACH1 Polyclonal Antibody, DACH1 Monoclonal Antibody (3B6D2), and the like. DACH1 Polyclonal Antibody and DACH1 Monoclonal Antibody (3B6D2), can be commercially obtained from THERMOFISHER SCIENTIFIC, INC. In one embodiment, the method may use propidium iodide (DNA content) and an anti-BrdU antibody (Abcam) as an immunohistochemical stain for determining an abundance of DACH1.

The method typically includes administering the immunohistochemical stains to a sample of the cancer cell(s) obtained from the subject, preferably a human subject. The sample may be obtained by any suitable means readily known by one of ordinary skill in the art. In some embodiments, the sample of the cancer cell(s) is obtained via a biopsy.

The method may include determining a sensitivity of the one or more cancer cells based on the determination of a deletion of the DACH1 gene from the one or more cancer cells. In some embodiments, the method determines a sensitivity of the one or more cancer cells based a lack of abundance of DACH1 protein. For example, the one or more cancer cells may be determined to have a sensitivity to certain anti-cancer compositions/pharmaceutical drugs based on a determination that an abundance of DACH1 has been reduced by about 20% or more. In some embodiments, a reduction in DACH1 protein of about 30% or more, about 40% or more, about 50% or more, about 60% or more, about 70% or more, about 80% or more, or about 90% or more is used a threshold to determine if the one or more cancer cells have a sensitivity to certain anti-cancer compositions/pharmaceutical drugs. The determination of a reduction in DACH1 protein may be based on the one or more cancer cells having a reduced or lower abundance of DACH1 protein as compared to non-cancer cells from (e.g., the same organ or tissue from) the same subject. In one embodiment, however, the determination of a reduction in DACH1 protein may be based on the one or more cancer cells having a reduced or lower abundance of DACH1 protein as compared to an average abundance of DACH1 protein in a human subject. Without being particularly limited to a specific theory, it is believed that when the DACH1 gene is deleted the DACH1 protein is absent from the one or more cancer cells and when the DACH1 gene is methylated there is a reduction in the abundance of DACH1 protein. For example, the level of DACH1 protein expression in tumors and normal human breast cancer in the TMAs was categorized by a semiquantitative score of the immunostaining intensity by light microscopy evaluation, using a standard methodology that determined a range of staining intensities from negative to strong with intermediate grades, with the intensity of immunoperoxidase staining being scored as 0 (negative), 1+ (a minimal to low level of positive staining), 2+ (moderate expression), or 3+ (strong staining). See Mol. Cell Biol. 2006 October; 26(19): 7116-7129. WU ET AL, which is incorporated herein by reference in its entirety for all purposes.

The one or more cancer cells may be determined to be sensitive to certain anti-cancer compositions and/or pharmaceutical treatments/drugs, such as a PARP inhibitor, (NAD-dependent or NAD independent), a chemotherapy from a DNA damaging agent, a TGFb inhibitor, a g irradiation (alone or in combination with a DNA-PK inhibitor), an androgen antagonist (e.g., flutamide), DNA-PK inhibitor(s), WEE1 inhibitor(s), prodrug(s) thereof, salt(s) thereof, or a combination of two or more thereof, based on the determination of the deletion of the DACH1 gene from the one or more cancer cells. The term "sensitive," as used herein, typically refers to a cancer cell being more readily targeted and/or vulnerable to being damaged or killed by certain treatments or pharmaceutical drugs. In at least one embodiment, the method may determine that a plurality of cancer cells (such as, prostate cancer cells, lung cancer cells, and/or breast cancer cells) have a sensitivity to DNA-PK inhibitors and/or WEE1 inhibitors based on the cancer cells having a deletion of the DACH1 gene. In yet additional embodiments, the method may determine that a plurality of cancer cells (such as, prostate cancer cells, lung cancer cells, and/or breast cancer cells) have a sensitivity to DNA-PK inhibitors and/or WEE1 inhibitors based on the cancer cells having a reduction in the abundance of the DACH1 protein(s). In a further embodiments, the method may determine that a plurality of cancer cells (such as, prostate cancer cells, lung cancer cells, and/or breast cancer cells) have a sensitivity to g-irradiation, chemotherapy, PARP inhibitors, DNA-PK inhibitors and/or WEE1 inhibitors based on the cancer cells having a reduction in the abundance of the DACH1 protein(s).

Additionally or alternatively, the method was surprisingly discovered to be able to determine a lack of sensitivity (e.g., a resistance) of one or more cancer cells to certain pharmaceutical treatments/drugs, such as Poly-(ADP-ribose) polymerases (PARPs) inhibitors, based on the determination of the deletion of the DACH1 gene from the one or more cancer cells, such as prostate, breast and/or lung cancer. In at least one embodiment, the method may further exclude or be free of the administration of PARP inhibitors based on a determination of the one or more cancer cells lacking sensitivity or being resistant to PARP inhibitors. Excluding or not administering PARP inhibitors to a subject having cancer cells that are resistant to PARP inhibitors can provide significant health benefits, as PARP inhibitors typically have adverse side effects.

PARPs are enzymes involved in DNA-damage repair. Inhibition of PARP is a promising strategy for targeting cancers with defective DNA-damage repair, including BRCA1 and BRCA2 mutation associated breast, ovarian and prostate cancer. Dose limiting side effects of PARPi are very serious and include gastrointestinal symptoms, anemia, and hematopoietic compromise. Several PARPi are currently in trials in a variety of malignancies including BRCA1-mutated breast cancer and prostate cancer. Accordingly, it was surprising that certain embodiments of the invention can determine the lack of sensitivity or resistance of certain cancers, such as those disclosed herein, to PARP inhibitors.

In some embodiments, e.g., where the cancer cell(s) are not resistant to PARP inhibitors, one or more PARP inhibitors may be administered. The PARP inhibitor may be a NAD-dependent or a NAD-independent PARP inhibitor. Examples of PARP inhibitors include niparib, olaparib, niraparib, rucparib, veliparib, BMN 673, CEP 9722, MK 4827, E 7016, 4-iodo-3-nitrobenzamide, benzamide, a metabolite thereof, or any combination of two or more thereof. In at least one embodiment, the NAD-dependent inhibitor is F502 and/or MC240022. Additional description of PARP inhibitors may be found in U.S. Pat. Nos. 7,732,491, 8,894,989, U.S. Patent Publication No. 2020/0129476, and U.S. Patent Publication No. 2015/0344968, all of which are incorporated herein by reference in their entirety for all purposes.

Figure 23A:
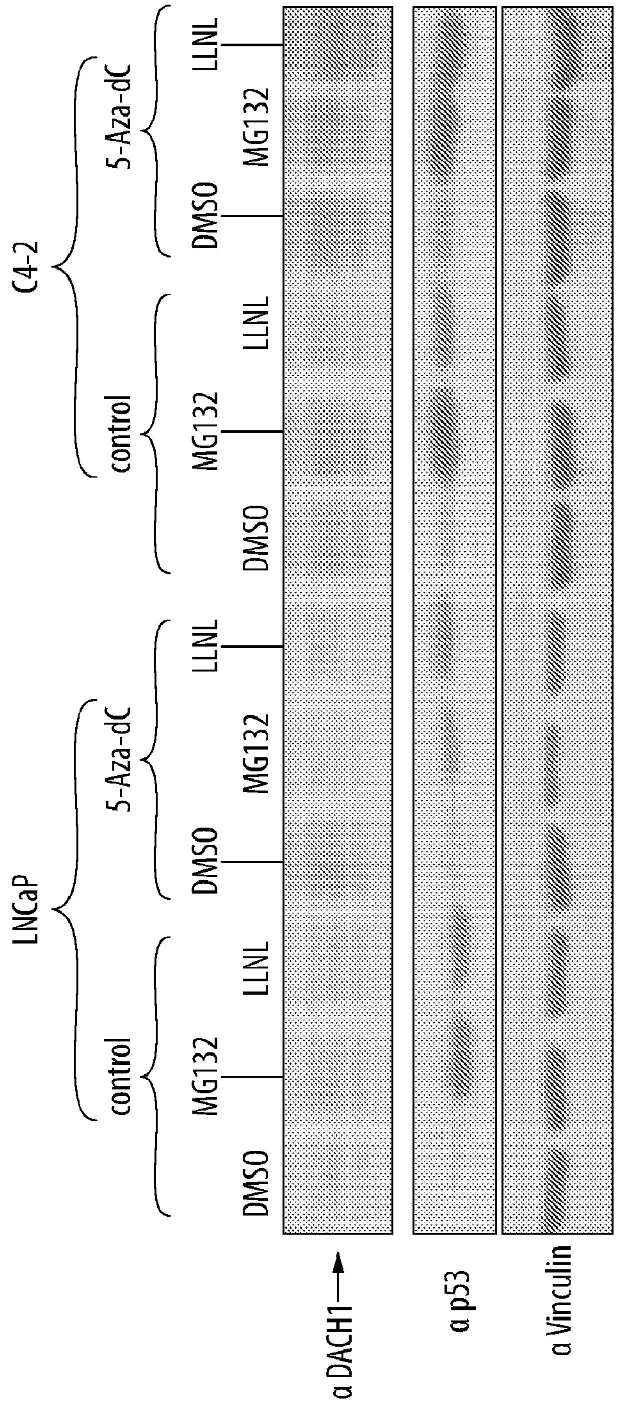
FIG. 23 is an image of a western blot LnCaP and C4-2 cells treated with the DNA methylase inhibitor 5-Aza-dC in accordance with aspects of the invention.
Figure 24B:
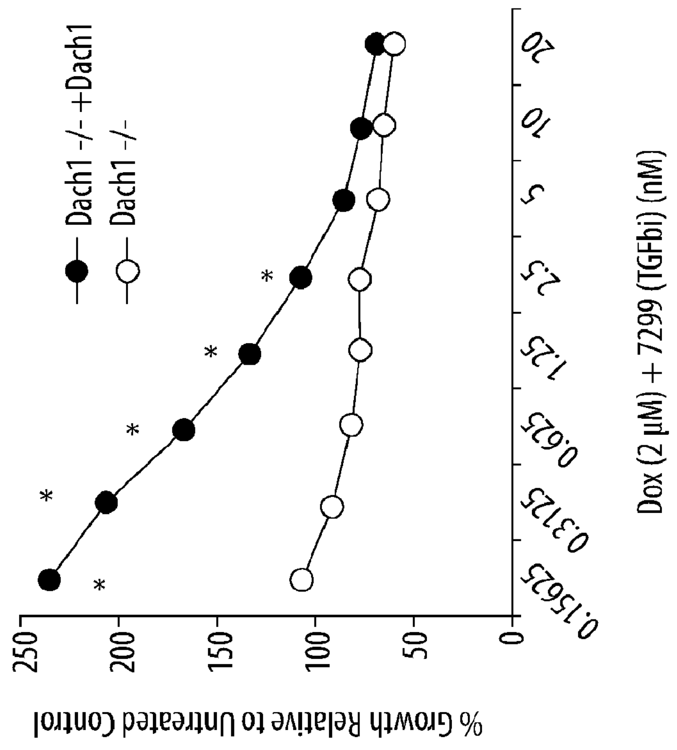
FIGS. 24A-24D are graphs of $DACH1^{-/-}$ 3T3 cells transduced with a DACH1 expression vector and treated with Doxorubicin and increasing doses of the TGF-b receptor type I (TGF-βRI) kinase inhibitors according to aspects of the invention.
Figure 24A:
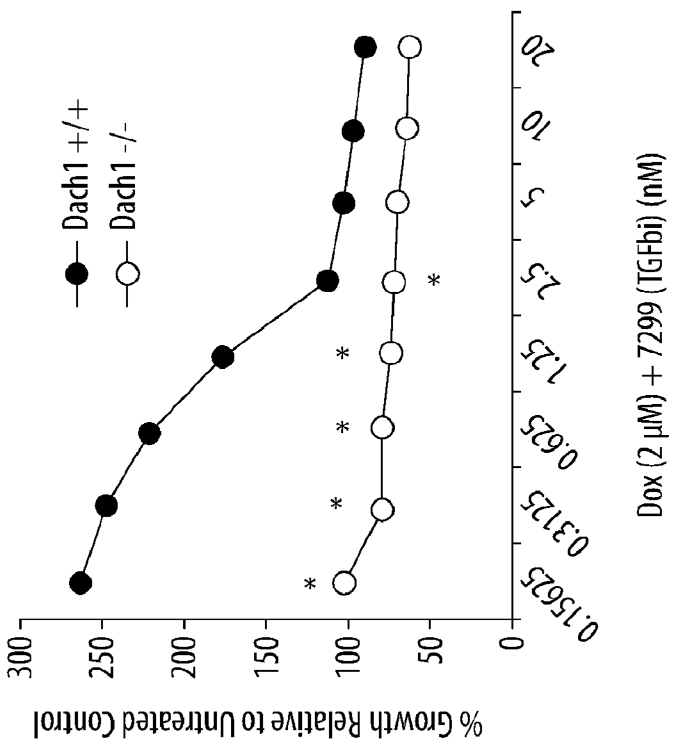
Figure 24C:
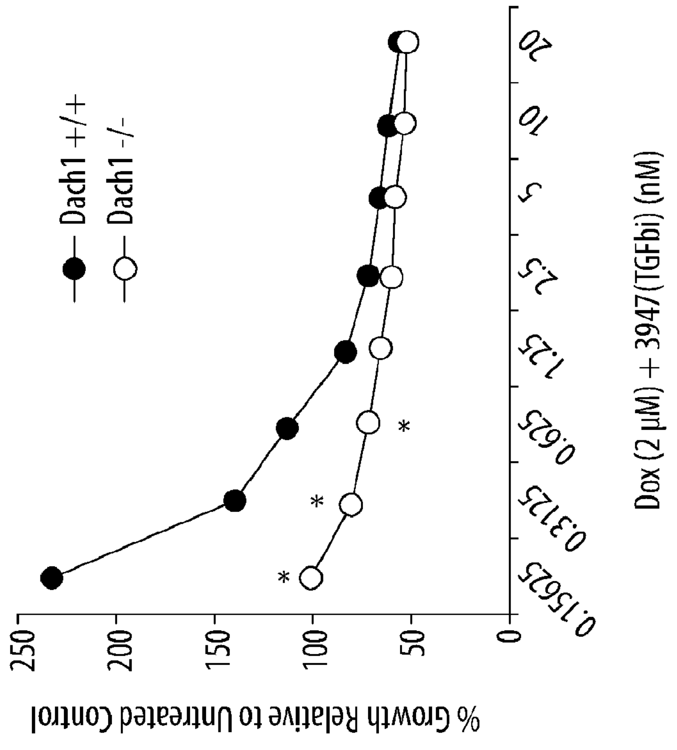
Figure 24D:
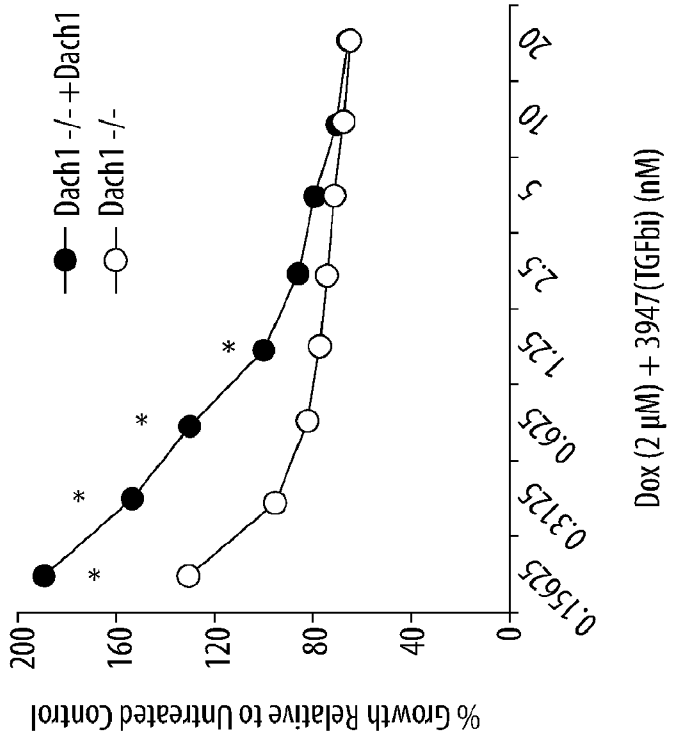

Additionally or alternatively, the method may include administering a DNA methylase inhibitor. The DNA methylase inhibitor may be administered before the administration of the administration of an immunohistochemical stains and/or before administering a composition comprising a PARP inhibitor, (NAD-dependent or NAD independent), a chemotherapy from a DNA damaging agent, a TGFb inhibitor, a g-irradiation (alone or in combination with a DNA-PK inhibitor), an androgen antagonist (e.g., flutamide), or combination of two or more thereof. Additional examples of DNA methylase inhibitor include 5-aza-2'-deoxycytidine, 5-azacytidine, 5-fuluoro-2'-deoxycytidine, 5,6-dihydro-5-azacytidine, zebularine, hydralazine, derivatives thereof, or a combination of two or more thereof. Derivatives obtained from known DNA methylase inhibitors subjected to alteration to a degree of not damaging effects thereof can be used as the DNA methylase inhibitor. In at least one embodiment, the DNA methylase inhibitor includes DNA methylase inhibitor, 5-Aza-dC, or a derivative thereof. As seen in FIG. 23, LnCaP and C4-2 cells were treated with the DNA methylase inhibitor 5-Aza-dC (10 μM, with either control, the 26S proteasome inhibitors MG132 (20 μM), or N-acetyl-L-leucyl-L-leucyl-L-nor leucinal (LLNL) (25 μM). The western blot, shown in FIG. 23, was conducted for the proteins indicated (DACH1, p53) and the protein loading control vinculin.

The method may also include administering a composition comprising a DNA-PK inhibitor, a WEE1 inhibitor, a prodrug thereof, a salt thereof, or a combination of two or more thereof if the one or more cancer cells are determined to be sensitive to DNA-PK inhibitor(s) and/or WEE1 inhibitor(s). In some embodiments, the method includes administering a composition comprising DNA-PK inhibitor, a WEE1 inhibitor, a prodrug thereof, a salt thereof, or a combination of two or more thereof if the one or more cancer cells are determined to have a deletion of the DACH1 gene.

According to another aspect of the invention, provided is a kit. The kit may include components for conducting the methods disclosed herein. For instance, the kit may include an immunohistochemical stain configured to determine the abundance of DACH1a gene product and equipment for administering the immunohistochemical stain. In some cases, the kit may include equipment for administering the immunohistochemical stain to one or more cells that have been removed from the subject; for example, via biopsy, blood sample, tissue sample, urine sample, stool sample, bone sample, and the like. Although the immunohistochemical stain may be administered to one or more cells removed from a human subject, in some instances the immunohistochemical stain is administered to a human subject. The immunohistochemical stain may be administered to the human subject by any of the means for administering a composition, such as those disclosed herein.

In some embodiments, the kits may also include one or more composition(s). For example, the kit may include a pharmaceutical composition comprising a DNA-PK inhibitor, a WEE1 inhibitor, a prodrug thereof, a salt thereof, or a combination of two or more thereof.

WEE1 is an essential tyrosine kinase recognized as a mitotic gatekeeper that phosphorylates and inactivates cyclin dependent kinase 1 (CDK1=CDC2), the only indispensable human cyclin dependent kinase. As cells transition into mitosis, WEE1 activity is reduced, allowing CDK1/cyclin B1 to initiate mitotic events. WEE1 is therefore important for properly timing cell division in unperturbed cells, and loss of WEE1 results in chromosomal aneuploidy and accumulated DNA damage. Additionally, WEE1 activity can be increased as a result of DNA damage, causing cells to arrest in G2 and allowing for repair of DNA lesions before beginning mitosis. It is believed that WEE1 is important for genomic integrity specifically as cells traverse S-phase, describing a previously unrecognized role for WEE1 in maintaining fidelity of DNA replication.

The methods and/or kits disclosed herein may utilize a WEE1 inhibitor, such as those having a structuring according to formula (I), a salt thereof, and/or a prodrug thereof.

(I)

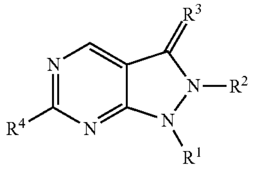

wherein:

$R^1$ is $C_{1-6}$ alkyl, aryl, or heteroaryl, that are optionally mono-, di-, or tri-substituted with $C_{1-6}$ alkyl, $C_{2-6}$ alkenyl, hydroxy, amino, amide, carboxylic acid, carboxylate ester, carbamate, hydrazide, hydroxamate, guanidino acetate, guanidine acetate esters, glycinate, or a combination thereof;

$R^2$ is H, $C_{1-6}$ alkyl, $C_{2-6}$ alkenyl, $C_{1-6}$ alkoxy, or $C_{1-6}$ alkyl optionally substituted with $C_{1-6}$ alkyl, hydroxy, amino, amide, carboxylic acid, carboxylate ester, aryl, substituted aryl, heteroaryl, or substituted heteroaryl;

$R^3$ is O, S, NH, $N^+HR$ 5 wherein $R^5$ is substituted or unsubstituted $C_{1-6}$ alkyl;

$R^4$ is $OR^6$ or $R^4$ is $NR^7R^8$ wherein $R^6$ is H, $C_{1-6}$ alkyl, $C_{3-8}$ cycloalkyl, benzamidyl, heterocycloalkyl, aryl or heteroaryl that are optionally mono-, di-, or tri-substituted with $C_{1-6}$ alkyl, $C_{2-6}$ alkenyl, hydroxy, amino, amide, carboxylic acid, carboxylate ester, $C_{1-6}$ alkylamino, ($C_{1-6}$ alkylamino) $C_{1-6}$ alkyl, ($C_{1-6}$ alkylamino)$C_{1-6}$ alkoxy, benzamidyl, heterocycloalkyl, substituted heterocycloalkyl, aryl, substituted aryl, heteroaryl, or substituted heteroaryl, or a combination thereof; and, wherein $R^7$ and $R^8$ are independently H, $C_{1-6}$ alkyl, $C_{3-8}$ cycloalkyl, benzamidyl, heterocycloalkyl, aryl or heteroaryl that are optionally mono-, di-, or tri-substituted with $C_{1-6}$ alkyl, $C_{2-6}$ alkenyl, hydroxy, amino, amide, carboxylic acid, carboxylate ester, $C_{1-6}$ alkylamino, ($C_{1-6}$ alkylamino)$C_{1-6}$ alkyl, ($C_{1-6}$ alkylamino)$C_{1-6}$ alkoxy, benzamidyl, heterocycloalkyl, substituted heterocycloalkyl, aryl, substituted aryl, heteroaryl, or substituted heteroaryl, or a combination thereof.

Further description of specific compounds having a structure in accordance with Formula (I), including methods of making and using thereof, may be found in US Patent Publication No. 2020/0405723, which is incorporated herein by reference, in its entirety, for all purposes.

AZD1775 (MK1775), aWEE1 kinase inhibitor, is potentially lethal in the context of ATRX deficiency. AZD1775 regresses H3K36me3-deficient tumor xenografts and sensitizes cells to immunotherapy. SETD2 restrains PCa metastasis and SETD2−/− cells are hypersensitive to AZD1775. The WEE1 inhibition may or may not be administered with a p53-activator.

WEE1-1, also known as +, is a potent (IC50=5.2 nM) and selective ATP-competitive small molecule inhibitor of WEE1.

WEE1-2 is a WEE1 inhibitor which may be useful for the treatment of cancers disclosed herein. WEE1-2 is also known as 3-(2,6-dichlorophenyl)-4-imino-7-[(2'-methyl-2',3'-dihydro-1'H-spiro[cyclopropane-1,4'-isoquinolin]-7'-yl) amino]-3,4-dihydropyrimido[4,5-d]pyrimidin-2(1H)-one. WEE1-2 has been described, including methods of making and using, in PCT International Publication No. WO 2008/153207 and US Patent Publication No. 2011/0135601, which are incorporated by reference herein in their entirety for all purposes. Crystalline forms of WEE1-2 are described in International Publication No. WO 2009/151997 and US Patent Publication No. 2011/0092520, which are incorporated by reference herein in their entirety for all purposes.

The methods and/or kits disclosed herein may utilize a DNA-PK inhibitor, such as those having a structuring according to formulas (II) or (III), or salts thereof.

(II)

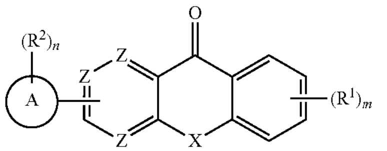

or

-continued (III)

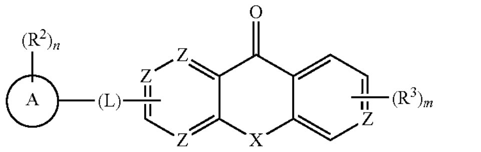

wherein, m is 0, 1, or 2;

n is 0 or 1;

X is O, $S(O)_{0-2}$, or $NR^a$;

Z, independently, is $CR^b$ or N;

L is absent, or L is selected from the group consisting of $—(CHR^h)_p—$, $—NR^h(CHR^h)_p—$, $—(CHR^h)—NR^h—NR^h$, $—C(—=O)—$, —O—, $—NR^h(CO)—$, $—(CO)NR^h—$, —S—, —SO—, $—SO_2—$, and $—NR^hR^q$, or $—O(SO_2)CF_3$ (provided A is absent), wherein p is an integer 1 to 5;

$R^h$ is selected from the group consisting of alkyl, aryl, and hydro;

$R^q$ is alkyl, optionally substituted with oxo, hydroxy, methoxy, benzyloxy, halo, aryl, or heteroaryl;

A is absent, or is heteroaryl or selected from the group consisting of a four- to seven-membered heterocyclic ring containing 1 or 2 heteroatoms independently selected from the group consisting of N and O;

m is 0, or $R^1$ is selected from the group consisting of halo, $CF_3$, $OR^d$, $OC_{1-3}alkyleneN(R^d)_2$, heterocycloalkyl, $N(R^d)C_{1-3}alkyleneN(R^d)_2$, $OP(=O)—(OR^d)_2$, $OP(=O)(ONa)_2$, substituted heterocycloalkyl, and $OC_{1-3}alkyleneC(=O)OR^d$;

n is 0, or $R^2$ is selected from the group consisting of OH, halo, $CH_2OH$, $C(=O)NH_2$, $NH_2$, $OCH_3$, $NHC(=O)CH_3$, $NHCH_3$, $NO_2$, $O(CH_2)_{1-3}OH$, O(C=O)heteroaryl, O(C=O)aryl, and O(C=O)alkyl;

$R^a$ is selected from the group consisting of hydro, $C_{1-4}$alkyl, aryl, heteroaryl, $C(=O)R^d$, $C(=O)—N(R^d)_2$, $SO_2R^d$, $SO_2N(R^d)_2$, and $C_{1-4}alkyleneOR^d$;

$R^b$, independently, is selected from the group consisting of hydro, OH, $OR^d$, $O(C_{1-3}alkylene)(=O)(OR^d)_2$, $O(C_{1-3}alkylene)(=O)(ONa)_2$, $OP(=O)—(OR^d)_2$, $OP(=O)(ONa)_2$, $NO_2$, $NH_2$, $NHR^d$, and halo.

In some cases, A is a morpholinyl, thiomorpholinyl, piperidinyl, piperazinyl, or tetrahydropyranyl group and L is absent. In at least one embodiment, the method includes administering the DNA-PK inhibitor, M3814.

Additionally or alternatively, the methods and/or kits disclosed herein may employ one or more DNA-targeted agents to be in administered with one or more pharmaceutical compound discussed herein. The DNA-targeted agents may be DNA alkylating agents and topoisomerase inhibitors, including cisplatin, capecitabine, carboplatin, cyclophosphamide, cytarabine, daunorubicin, docetaxel, doxorubicin, 5-fluorouracil, gemcitabine, methotrexate, paclitaxel, premetrexed, irinotecan temozolomide, topotecan, radiation, or a combination of two or more thereof. The methods and/or kits may employ one or more of the following compounds: cisplatin, cytarabine, temozolomide, doxorubicin, Bcl-2 inhibitors (such as ABT199), or a combination of two or more thereof.

In some cases, the methods and/or kits disclosed herein may employ a chemotherapy or a chemo-immunotherapy. The chemotherapies may include a chemotherapeutic agent selected from alkylating agents, anti-metabolitic agents, antibiotics, anti-tubule agents, anti-hormonal agents, and combinations of two or more thereof. Examples of chemotherapeutic agents include, but not limited to mechlorethamine (Embichin), cyclophosphamide (Endoxan), Myleran (Busulfan), chlorambucil, leukeran, paraplatin, cisplatin, carboplatin, platinol, Methotrexate (MTX), 6-mercaptopurine (6-MP), cytarabine (Ara-C), floxuridine (FUDR), fluorouracil (Adrucil), hydroxyurea (Hydrea), etoposide (VP16), actinomycin D, bleomycin, mithramycin, daunorubicin, taxol and its derivatives, vinca and its derivatives, bicalutamide (Casodex), Flutamide (Eulixin), Tamoxifen (Noluadex), Megestrol (Magace), and combinations thereof.

Chemo-immunotherapies using cytotoxic drugs and cytokines offers a new approach for improving the treatment of neoplastic diseases. The therapeutic efficacy of combinations of IL-12 proteins with cyclophosphamide, paclitaxel, cisplatin or doxorubicin has been investigated in the murine L1210 leukemia model. See *Int. J. Cancer,* 1998, vol. 77, 720, which is incorporated herein by reference in its entirety for all purposes. Treatment of L1210 leukemia with IL-12 or one of the above chemotherapeutic agents given alone resulted in moderate antileukemic effects. Combination of IL-12 with cyclophosphamide or paclitaxel produced no augmentation of antileukemic effects in comparison with these agents given alone. In combination with chemotherapy, IL-12 may be administered to increase antitumor activity without causing additional toxicity. Disclosures of chemotherapies and/or chemo-immunotherapies may be found in U.S. Pat. Nos. 8,623,837, 11,040,042, 9,839,638, 10,300,076, 9,040,574, and 7,930104, all of which are incorporated herein by reference in their entireties for all purposes.

The method may, optionally, include administering of irradiation to the one or more cancer cells. Preferably, the radiation is gamma irradiation (g-irradiation) or proton irradiation. The administration of radiation may be enhanced using certain compounds, such as those described in U.S. Patent Publication No. 20100168038, which is incorporated herein by reference in its entirety for all purposes. Disclosures relating to the use of irradiation of cancer cells can be found in U.S. Patent Publication No. 2017/0355778, U.S. Pat. Nos. 10,213,625, and 8,569,717, all of which are incorporated herein by reference in their entirety for all purposes.

The methods and/or kits disclosed herein may include DNA-PK inhibitor(s), WEE1 inhibitor(s), prodrug(s) thereof, salt(s) thereof, or a combination of two or more thereof contained in a composition, e.g., a pharmaceutical composition. The composition comprising the DNA-PK inhibitor(s), WEE1 inhibitor(s), salt(s) thereof, and/or prodrug(s) thereof may include a therapeutically effective amount of DNA-PK and/or WEE1 inhibitor(s). The "Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid, and the like.

"Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66: 1 (1977).

As used herein "therapeutically effective amount" or "therapeutically effective dosage" refers to an amount that is effective to achieve a desired therapeutic result, such as inhibition of angiogenesis or an anti-tumor or anti-metastatic effect, inhibition of TNF-α activity, inhibition of immune cytokines, or treatment of a neurodegenerative disease. In some embodiments, the desired therapeutic result is a reduction in the growth of cancer cells and/or reduction in the likelihood of metastasizing. In further embodiments, a therapeutically effective amount is an amount sufficient to achieve tissue concentrations at the site of action that are similar to those that are shown to modulate angiogenesis, TNF-α activity, or immune cytokines, in tissue culture, in vitro, or in vivo. For example, a therapeutically effective amount of a compound may be such that the subject receives a dosage of about 0.1 μg/kg body weight/day to about 1000 mg/kg body weight/day, for example, a dosage of about 1 μg/kg body weight/day to about 1000 μg/kg body weight/day, such as a dosage of about 5 μg/kg body weight/day to about 500 μg/kg body weight/day.

In some cases, the amount of DNA-PK inhibitor, WEE1 inhibitor, prodrug thereof, salt thereof, or a combination of two or more thereof present in composition is more than about 1 μg. For example, the composition may comprise an amount of DNA-PK inhibitor, WEE1 inhibitor, prodrug thereof, salt thereof, or a combination of two or more thereof of about 2 μg or more, about 5 μg or more, about 10 μg or more, about 100 μg or more, about 500 μg or more, about 1000 μg or more, about 1500 μg or more, about 2000 μg or more, about 2500 μg or more, about 3000 μg or more, about 3500 μg or more, about 4000 μg or more, about 4500 μg or more, about 5000 μg or more, about 5500 μg or more, about 6000 μg or more, about 6500 μg or more, about 7000 μg or more, about 7500 μg or more, about 8000 μg or more, about 8500 μg or more, about 9000 μg or more, about 9500 μg or more, about 10 mg or more, about 20 mg or more, about 30 mg or more, about 40 mg or more, about 50 mg or more, about 60 mg or more, about 70 mg or more, about 80 mg or more, about 90 mg or more, about 100 mg or more, about 150 mg or more, about 200 mg or more, about 250 mg or more, about 300 mg or more, about 350 mg or more, about 400 mg or more, about 450 mg or more, about 500 mg or more, about 550 mg or more, about 600 mg or more, about 650 mg or more, about 700 mg or more, about 800 mg or more, about 900 mg or more, or about 1 g or more. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

Additionally or alternatively, the amount of DNA-PK inhibitor, WEE1 inhibitor, prodrug thereof, salt thereof, or a combination of two or more thereof present in the composition may be about 0.01 wt. % to about 95 wt. %, about 0.1 wt. % to about 95 wt. %, about 1 wt. % to about 95 wt. %, about 5 wt. % to about 95 wt. %, about 10 wt. % to about 95 wt. %, about 15 wt. % to about 90 wt. %, about 20 wt. % to about 95 wt. %, about 30 wt. % to about 95 wt. %, about 40 wt. % to about 95 wt. %, about 50 wt. % to about 95 wt. %, about 60 wt. % to about 95 wt. %, about 70 wt. % to about 95 wt. %, about 80 wt. % to about 95 wt. %; about 0.01 wt. % to about 85 wt. %, about 0.1 wt. % to about 85 wt. %, about 1 wt. % to about 85 wt. %, about 5 wt. % to about 85 wt. %, about 10 wt. % to about 85 wt. %, about 15 wt. % to about 85 wt. %, about 20 wt. % to about 85 wt. %, about 30 wt. % to about 85 wt. %, about 40 wt. % to about 85 wt. %, about 50 wt. % to about 85 wt. %, about 60 wt. % to about 85 wt. %, about 70 wt. % to about 85 wt. %; about 0.01 wt. % to about 75 wt. % about 0.1 wt. % to about 75 wt. %, about 1 wt. % to about 75 wt. %, about 5 wt. % to about 75 wt. %, about 10 wt. % to about 75 wt. %, about 15 wt. % to about 75 wt. %, about 20 wt. % to about 75 wt. %, about 30 wt. % to about 75 wt. %, about 40 wt. % to about 75 wt. %, about 50 wt. % to about 75 wt. %, about 60 wt. % to about 75 wt. %; about 0.01 wt. % to about 65 wt. %, about 0.1 wt. % to about 65 wt. %, about 1 wt. % to about 65 wt. %, about 5 wt. % to about 65 wt. %, about 10 wt. % to about 65 wt. %, about 15 wt. % to about 65 wt. %, about 20 wt. % to about 65 wt. %, about 30 wt. % to about 65 wt. %, about 40 wt. % to about 65 wt. %, about 50 wt. % to about 65 wt. %; about 0.01 wt. % to about 55 wt. %, about 0.1 wt. % to about 55 wt. %, about 1 wt. % to about 55 wt. %, about 5 wt. % to about 55 wt. %, about 10 wt. % to about 55 wt. %, about 15 wt. % to about 55 wt. %, about 20 wt. % to about 55 wt. %, about 30 wt. % to about 55 wt. %, about 40 wt. % to about 55 wt. %; about 0.01 wt. % to about 45 wt. %, about 0.1 wt. % to about 45 wt. %, about 1 wt. % to about 45 wt. %, about 5 wt. % to about 45 wt. %, about 10 wt. % to about 45 wt. %, about 15 wt. % to about 45 wt. %, about 20 wt. % to about 45 wt. %, about 30 wt. % to about 45 wt. %; about 0.01 wt. % to about 35 wt. %, about 0.1 wt. % to about 35 wt. %, about 1 wt. % to about 35 wt. %, about 5 wt. % to about 35 wt. %, about 10 wt. % to about 35 wt. %, about 15 wt. % to about 35 wt. %, about 20 wt. % to about 35 wt. %; about 0.01 wt. % to about 25 wt. %, about 0.1 wt. % to about 25 wt. %, about 1 wt. % to about 25 wt. %, about 5 wt. % to about 25 wt. %, about 10 wt. % to about 25 wt. %; about 0.1 wt. % to about 15 wt. %, about 1 wt. % to about 15 wt. %, about 5 wt. % to about 15 wt. %, about 10 wt. % to about 15 wt. %; about 0.01 wt. % to about 25 wt. %, about 0.1 wt. % to about 10 wt. %, about 1 wt. % to about 10 wt. %, or about 5 wt. % to about 10 wt. %, including ranges and subranges thereof, based on the total weight of the composition.

Additionally or alternatively, the compositions may be formulated to have a weight ratio of DNA-PK inhibitor to WEE1 inhibitor (or therapeutically effective amounts thereof) of 1:100 to 100:1, 1:50 to 50:1, 1:20 to 20:1 1:10 to 10:1, 1:9 to 10:1, 1:8 to 10:1, 1:7 to 10:1, 1:6 to 10:1, 1:5 to 10:1, 1:4 to 10:1, 1:3 to 10:1, 1:2 to 10:1, 1:1 to 10:1, 1:10 to 9:1, 1:10 to 8:1, 1:10 to 7:1, 1:10 to 6:1, 1:10 to 5:1, 1:10 to 4:1, 1:10 to 3:1, 1:10 to 2:1, or 1:10 to 1:1, including ranges and subranges thereof. One of ordinary skill would be able to prepare the compositions disclosed herein using known methods and/or in the art in view of the disclosure herein.

The compositions typically further comprise at least one excipient. Suitable excipients include pharmaceutically acceptable excipients, such as diluents, binders, fillers, buffering agents, pH modifying agents, disintegrants, dispersants, preservatives, lubricants, taste-masking agents, flavoring agents, coloring agents, or combinations thereof. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl pa lmitate, citric acid, sodium citrate; chelators such as EDTA or EGTA; and antimicrobials, such as parabens, chlorobutanol, or phenol.

In a further embodiment, the excipient may be a lubricant. Nonlimiting examples of suitable lubricants include minerals such as talc or silica; and fats such as vegetable stearin, magnesium stearate, or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2% or less, or about 1% or less of the total weight of the composition.

The composition may be formulated into various dosage forms and administered by a number of different means that will deliver a therapeutically effective amount of the active ingredient. Such compositions may be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term, "parenteral," as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, the composition may be a food supplement or a cosmetic.

Solid dosage forms for oral administration may be contained in capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfate; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, suspensions, or creams as generally known in the art.

In certain embodiments, a composition may comprise a compound that is encapsulated in a suitable vehicle to either aid in the delivery of such compound to target cells, to increase the stability of the composition, or to minimize potential toxicity of the composition. As will be appreciated by a skilled artisan, a variety of vehicles are suitable for delivering a composition of the present invention. Non-limiting examples of structured fluid delivery systems may include nanoparticles, liposomes, microemulsions, micelles, dendrimers, and other phospholipid-containing systems. Methods of incorporating compositions into delivery vehicles are known in the art. Disclosures relating to the administration of compositions using nanotechnology and/or nano drug delivery systems are described in U.S. Pat. No. 7,491,407, U.S. Patent Publication No. 2013/0225412, U.S. Pat. No. 9,180,102, which are all incorporated herein by reference in their entirety for all purposes.

In one alternative embodiment, a liposome delivery vehicle may be utilized. Liposomes, depending upon the embodiment, may be used for delivery of a composition comprising DNA-PK inhibitor, WEE1 inhibitor, prodrug thereof, salt thereof, or a combination of two or more thereof in view of their structural and chemical properties. Generally, liposomes are spherical vesicles with a phospholipid bilayer membrane. The lipid bilayer of a liposome may fuse with other bilayers (e.g., the cell membrane), thus delivering the contents of the liposome to cells.

Liposomes may be comprised of a variety of different types of phosolipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,T-dedodecyl-3,3,3',3'-tetramethylindocarbocyanine perchloarate, 1,T-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetro nitrile, alcohols, dimethylformamide, tetrahydrofuran, or combinations thereof.

Liposomes carrying a composition disclosed herein may be prepared by any known method of preparing liposomes for drug delivery, such as, for example, detailed in U.S. Pat. Nos. 4,241,046, 4,394,448, 4,529,561, 4,755,388, 4,828, 837, 4,925,661, 4,954,345, 4,957,735, 5,043,164, 5,064,655, 5,077,211, and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration, and composition of lipid, concentration of multivalent cations, rate of mixing, presence of and concentration of solvent.

The composition may be formulated as part of a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids.

Any of the phospholipids detailed above for liposomes are suitable for embodiments directed to microemulsions. A composition comprising at least one anti-viral therapeutic derivative may be encapsulated in a microemulsion by any method generally known in the art.

In yet another embodiment, the composition may contain compounds delivered in a dendritic macromolecule, or a dendrimer. Generally, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

The methods of the disclosure may include administering an amount of a composition topically, orally, or parenterally. For oral administration, the method may include administering an amount of the composition in the form of a solid dosage or a liquid dosage. Solid dosage forms for oral administration include capsules, tablets, caplets, pills, powders, pellets, and granules. Liquid dosages of the composition may be in the form of aqueous suspensions, elixirs, or syrups. For these, the composition may be combined with various sweetening or flavoring agents, coloring agents, and, if so desired, emulsifying and/or suspending agents, as well as diluents such as water, ethanol, glycerin, and combinations thereof.

For parenteral administration, the dosage of composition may be an aqueous solution, an oil-based solution, or in the form of a solid dosage. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfate; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. In some instances, parental administration may be subcutaneous, intravenous, intramuscular, or intrasternal injection, or infusion.

In accordance with another aspect of the invention, provided is a method for employing transgenic mouse model. The method typically comprises obtaining transgenic cells from a transgenic mouse containing human DNA; inducing Cre recombinase in the transgenic cells using photo-uncaging; and determine a deletion of the DACH1 gene in the transgenic cells. The method may further includes determining one or more cell functions dependent upon the DACH1 gene deletion. In some embodiments, the method comprises promoting the production of Ku70 and/or Ku80 proteins in the transgenic cells. The Ku70 and/or Ku80 proteins may be promoted using laser irradiation. Additionally or alternatively, the method may include conducting cell line implantation to implant a plurality of the transgenic cells determined to have a deletion of the DACH1 gene into an immune deficient mouse. In one preferred embodiment, the transgenic cells are human prostate cancer cells, human lung cancer cells, and/or human breast cancer cells.

The term "alkyl" and "alkylene" as used herein refer to straight- and branched-chain hydrocarbon groups, preferably containing one to sixteen carbon atoms. Examples of alkyl groups are $C_{1-4}$alkyl groups. As used herein the designation $C_{x-y}$, wherein x and y are integers, denotes a group having from x to y carbons, e.g., a $C_{1-4}$alkyl group is an alkyl group having one to four carbon atoms. Nonlimiting examples of alkyl groups include, but are not limited to, methyl, ethyl, n-propyl, isopropyl, n-butyl, sec-butyl (2-methylpropyl), t-butyl (1,1-dimethylethyl), and the like. Nonlimiting examples of alkylene groups include methylene ($—CH_2—$) and ethylene ($—CH_2CH_2—$).

The term "cycloalkyl" as used herein refers to an aliphatic cyclic hydrocarbon group, preferably containing three to eight carbon atoms. Nonlimiting examples of cycloalkyl groups include cyclopropyl, cyclobutyl, cyclopentyl, cyclohexyl, and the like.

The terms "substituted alkyl," "substituted cycloalkyl," and "substituted alkylene" as used herein refer to an alkyl, cycloalkyl, or alkylene group having one or more substituents. The substituents include, but are not limited to, cycloalkyl, aryl, heteroaryl, heterocycloalkyl, substituted aryl, substituted heteroaryl, substituted heterocycloalkyl, $N(R^d)_2$, $OR^d$, $SR^d$, sulfoxide, sulfonyl, halo, carboxyl, acyl, carboxy, hydrazino, hydrazono, and hydroxyamino. The preferred substituted alkyl groups have one to four carbon atoms, not including carbon atoms of the substituent group. Preferably, a substituted alkyl group is mono- or di-substituted at one, two, or three carbon atoms. The substituents can be bound to the same carbon or different carbon atoms.

The term "alkoxy" as used herein refers to a straight- or branched-chain alkyl, optionally substituted, group attached to the parent molecule through an oxygen atom, typically by a carbon to oxygen bond, i.e., —OR, wherein R is an alkyl group. The hydrocarbon group of the alkoxy group preferably contains one to four carbon atoms. Typical alkoxy groups include, but are not limited to, methoxy, ethoxy, n-propoxy, isopropoxy, n-butoxy, sec-butoxy, t-butoxy, and the like. The term "thioalkoxy" is similarly defined, except sulfur replaces oxygen.

The term "acyl" as used herein refers to a $R^eC(=O)$ group attached to the parent molecule through a carbonyl ($C=O$) group. $R^e$ is selected from the group consisting of alkyl, substituted alkyl, cycloalkyl, substituted cycloalkyl, aryl, substituted aryl, heteroaryl, substituted heteroaryl, heterocycloalkyl, and substituted heterocycloalkyl groups.

The term, "aryl" as used herein refers to monocyclic, fused bicyclic, and fused tricyclic carbocyclic aromatic ring systems including, but not limited to, phenyl, naphthyl, tetrahydronaphthyl, phenanthrenyl, biphenylenyl, indanyl, indenyl, anthracenyl, fluorenyl, and the like.

The term "heteroaryl" as used herein refers to monocyclic, fused bicyclic, and fused tricyclic aromatic ring systems, wherein one to four-ring atoms are selected from the group consisting of oxygen, nitrogen, and sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, thiophenyl, furanyl, quinolinyl, isoquinolinyl, benzoxazolyl, benzimidazolyl, benzothiazolyl, and the like.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl groups ring systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, and the like.

The terms "substituted aryl," "substituted heteroaryl," and "substituted heterocycloalkyl" as used herein refer to an aryl, heteroaryl, or heterocycloalkyl group substituted by a replacement of one, two, or three of the hydrogen atoms thereon with a substitute selected from the group consisting of halo, $OR^d$, $N(R^d)_2$, $C(=O)N(R^d)_2$, CN, alkyl, substituted alkyl, mercapto, nitro, aldehyde, carboxy, carboxyl, carboxamide, aryl, substituted aryl, heteroaryl, substituted heteroaryl, cycloalkyl, substituted cycloalkyl, heterocycloalkyl, substituted heterocycloalkyl, $O(CH_2)_{1-3}N(R^d)_2$, $O(CH_2)_{1-3}CO_2H$, and trifluoromethyl.

The term "aldehyde" as used herein refers to a —CHO group.

The term "amino" as used herein refers an $—NH_2$ or —NH— group, wherein each hydrogen in each formula can be replaced with an alkyl, cycloalkyl, aryl, heteroaryl, heterocycloalkyl, substituted alkyl, substituted cycloalkyl, substituted aryl, substituted heteroaryl, or substituted heterocycloalkyl group, i.e., $N(R^e)_2$. In the case of $—NH_2$, the hydrogen atoms also can be replaced with substituents taken together to form a 5- or 6-membered aromatic or nonaromatic ring, wherein one or two carbons of the ring optionally are replaced with a heteroatom selected from the group consisting of sulfur, oxygen, and nitrogen. The ring also optionally can be substituted with an alkyl group. Examples of rings formed by substituents taken together with the nitrogen atom include, but are not limited to, morpholinyl, phenylpiperazinyl, imidazolyl, pyrrolidinyl, (N-methyl)piperazinyl, piperidinyl, and the like.

The term "carbamoyl" as used herein refers to a group of the formula $NR^d(=O)R^d$, $—OC(=O)N(R^d)_2$, and $—NR^dC(=O)—$, wherein R d is defined above.

The term "carbonyl" as used herein refers to a CO, C(O), or $C(=O)$ group.

The term "carboxyl" as used herein refers to $—CO_2H$.

The term "carboxy" as used herein refers to a $—COOR^d$, wherein $R^d$ is defined above.

The term "carboxamide" as used herein refers to $—C(=O)N(R^g)_2$, wherein $R^g$ is defined as hydro, alkyl, substituted alkyl, aryl, substituted aryl, heteroaryl, substituted heteroaryl, heterocycloalkyl, substituted heterocycloalkyl, cycloalkyl, substituted cycloalkyl, or $OR^d$, or the $R^g$ groups are taken together with the nitrogen to which they are attached to form a five- or six-membered optionally substituted aromatic or nonaromatic ring, wherein one or two carbons of the ring optionally are replaced with a heteroatom selected from the group consisting of sulfur, oxygen, and nitrogen.

The term "thiocarboxamide" as used herein, refers to $—C(=S)N(R^g)_2$, wherein $R^g$ is defined above.

The term "mercapto" as used herein refers to $—SR^d$, wherein $R^d$ is defined above.

The term "sulfonamido" as used herein refers to $—NHSO_2R^g$, wherein $R^g$ is defined above.

The term “cyano” as used herein refers to a —C≡N group, also designated —CN.

The term “hydroxyamino” as used herein refers to a —NHOH group.

The term “hydrazono” as used herein refers to a =N—$NH_2$ group, wherein one or both hydrogen atoms can be replaced with an alkyl or substituted alkyl group.

The terms “trifluoromethyl” and “trifluoromethoxy” as used herein refer to —$CF_3$ and —$OCF_3$, respectively.

The term “halo” as used herein refers to bromo, chloro, iodo, and fluoro.

The term “sulfonyl” as used herein refers to group represented by —$SO_2$— or —$SO_2R^d$, wherein $R^d$ is defined above.

The term “sulfamyl” as used herein refers to —$SO_2N(R^g)_2$, wherein $R^g$ is defined above.

The term “sulfa” as used herein refers to —$SO_3H$.

The term “nitro” as used herein refers to —$NO_2$.

In the structures herein, for a bond lacking a substituent, the substituent is methyl, for example,

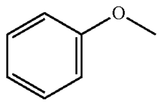
is
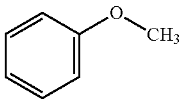

When no substituent is indicated as attached to a carbon atom on a ring, it is understood that the carbon atom contains the appropriate number of hydrogen atoms. In addition, when no substituent is indicated as attached to a carbonyl group or a nitrogen atom, for example, the substituent is understood to be hydrogen, e.g.,

is
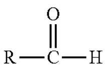
and R—N is R—$NH_2$

The abbreviation “Me” is methyl and Bn is benzyl.

The notation $N(Rx)_2$, wherein x represents an alpha or numeric character, such as, for example, R d is used to denote two Rx groups attached to a common nitrogen atom. When used in such notation, the RX group can be the same or different, and is selected from the group as defined by the Rx group.

EXAMPLES

Example 1

Figure 5A:
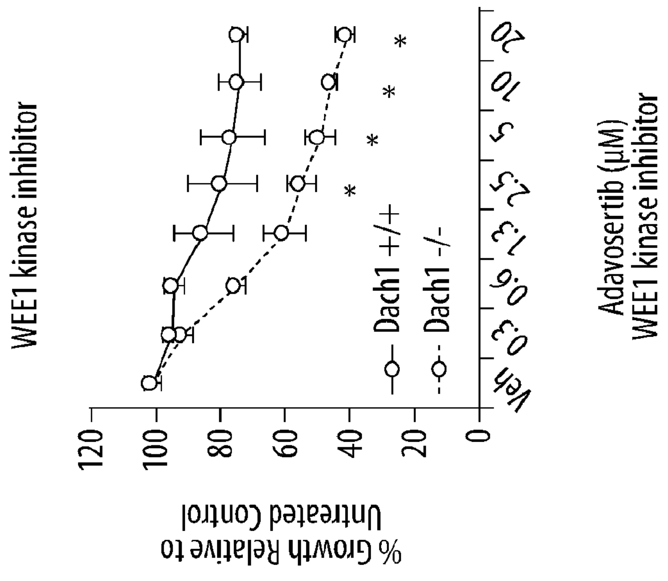
FIGS. 5A and 5B are graphs showing that DACH1 deficiency effects cancer cells sensitivity to WEE1 kinase inhibitors in accordance with aspects of the invention.
Figure 5B:
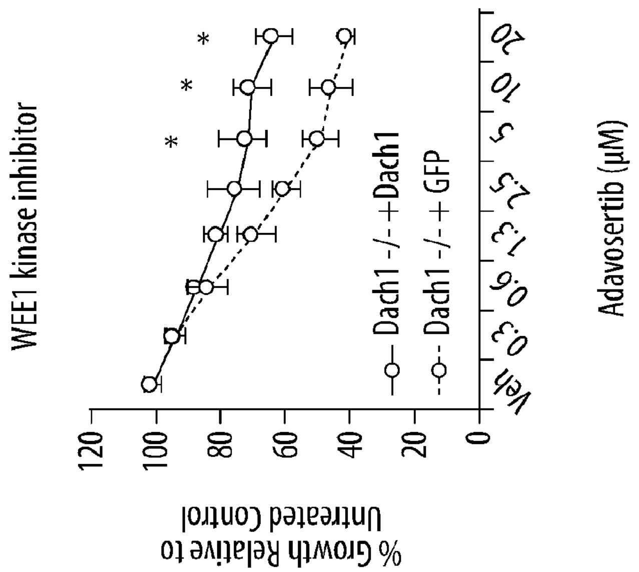

DACH1 deficiency was determined to effect sensitivity of cancer cells to WEE1 kinase inhibitors. As seen in FIG. 5A, 3T3 cells were treated for 72 h with increasing dose of Adavosertib, a small molecule inhibitor of the tyrosine kinase WEE1, and the effect on cell growth was determined. Additionally, 3T3 cells were transfected with a mammalian expression vector for DACH1 or with control vector and growth sensitivity to Adavosertib assessed after 72 hrs (see FIG. 5B). Data in FIGS. 5A and 5B are shown as mean±SEM for 3 separate experiments (9 replicate data points).

Example 2

Figure 6:
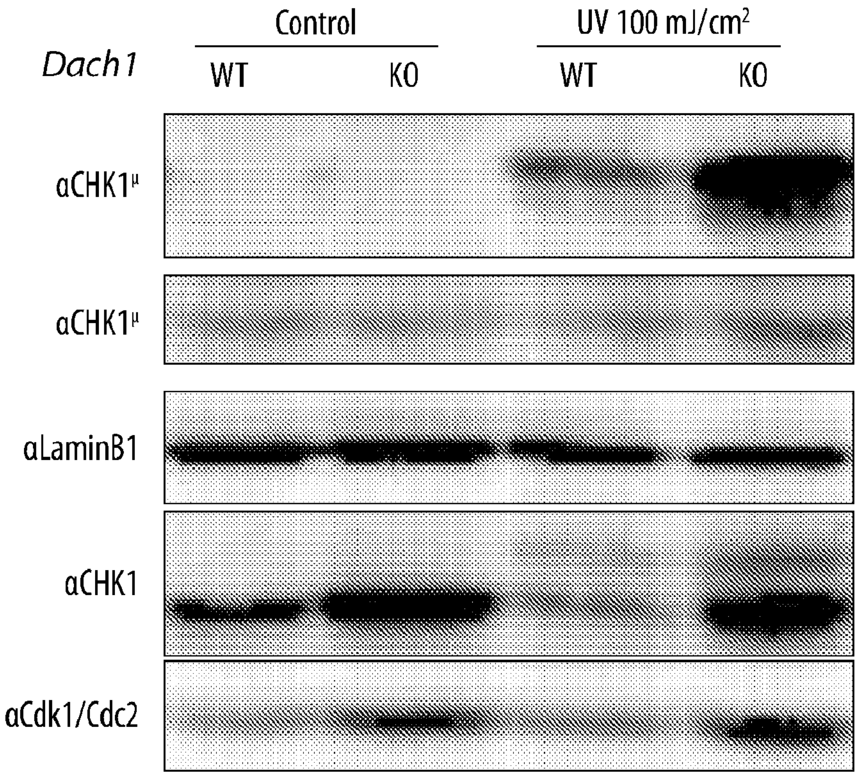
FIG. 6 presents graphs showing that DACH1 expression governs CHK1 and CDK1 phosphorylation according to aspects of the invention.

DACH1 expression was determined to govern Chk1 and CDK1 phosphorylation. As seen in FIG. 6, western blot analysis of DACH1$^{-/-}$ 3T3 cells were treated with UV radiation (100 mJ/$cm^2$). The western blot was conducted for the proteins indicated and a protein loading control, namely Lamin B1.

Example 3

Figure 7A:
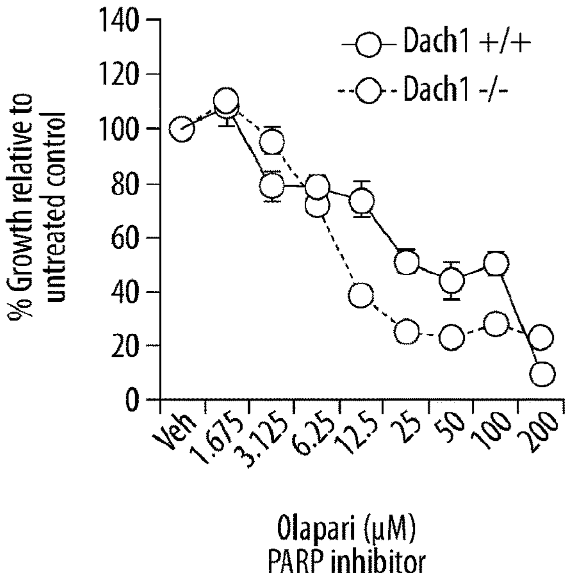
FIGS. 7A-7C are graphs showing that DACH1 deficiency effects resistance to PARP inhibitors in accordance with aspects of the invention.
Figure 7B:
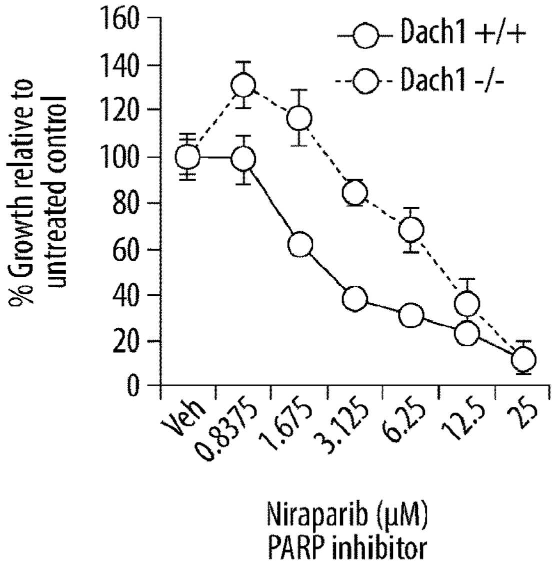
Figure 7C:
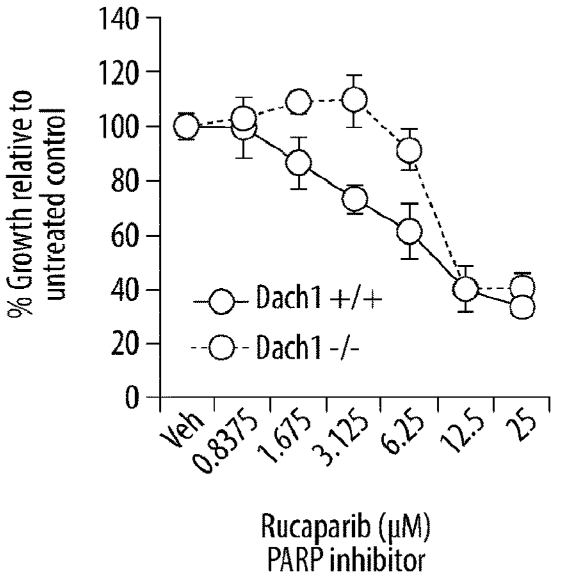

DACH1 deficiency was determined to effect resistance to PARP inhibitors. 3T3 cells were treated for 72 h with increasing dose of PARPi (see FIG. 7A), Olaparib (see FIG. B), or Niraparib (see FIG. 7C). Rucaparib and the effect on cell growth was determined. The data in FIGS. 7A-7C are shown as mean±SEM for 5 separate experiments (15 replicate data points).

Example 4

Figure 8A:
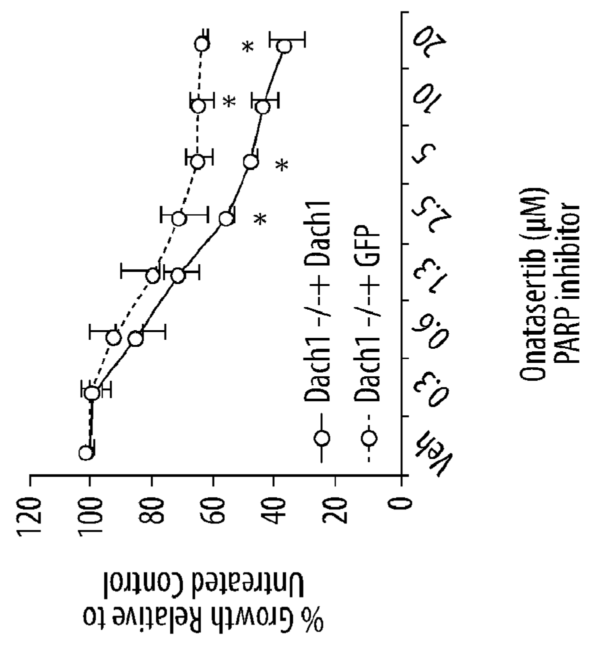
FIGS. 8A and 8B are graphs showing the sensitivity of DACH1$^{-/-}$ 3T3 cells to increasing dose of Onatasertib or Talazoparib, respectively, according to aspects of the invention.
Figure 8B:
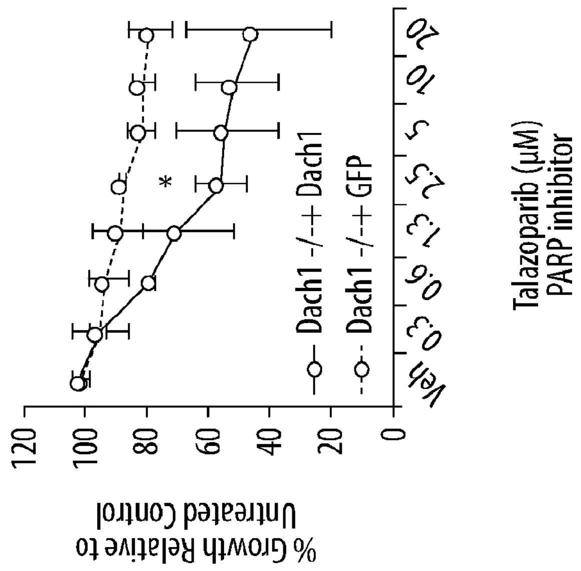

DACH1 deficiency effects resistance to PARP inhibitors. DACH1$^{-/-}$ 3T3 cells were transfected with a mammalian expression vector for DACH1 or with control vector with GFP. FIGS. 8A and 8B show the sensitivity to increasing dose of onatasertib (see FIG. 8A) or Talazoparib (see FIG. 8B) after 72 h, both of which are PARP inhibitors. The data is shown in FIGS. 8A and 8B as mean±SEM for 3 separate experiments (9 replicate data points).

Example 5

Figure 9A:
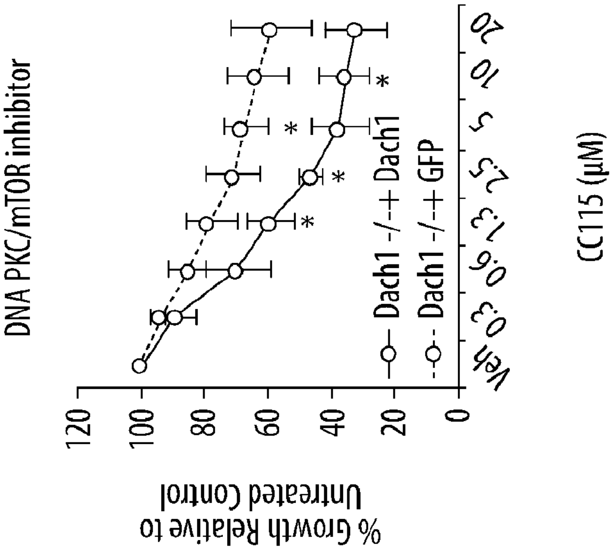
FIGS. 9A and 9B are graphs showing the sensitivity of DACH1$^{-/-}$ 3T3 cells to increasing dose of CC115 or VX-984, respectively, in according to aspects of the invention.
Figure 9B:
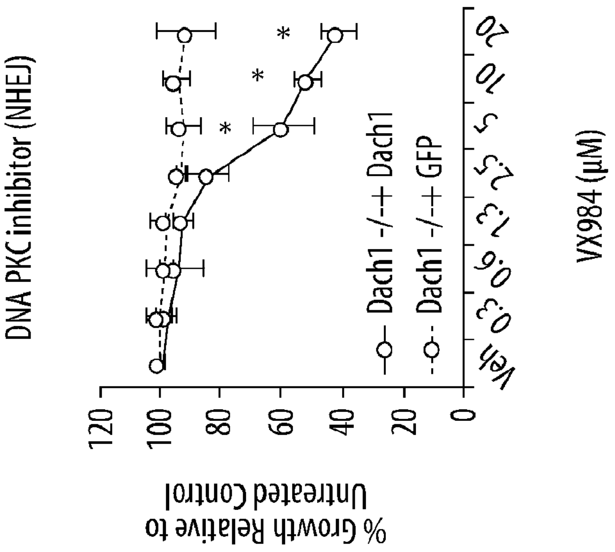

DACH1 deficiency was determined to effect resistance to DNA-PKC/mTOR inhibitors. DACH1$^{-/-}$ 3T3 cells were transfected with a mammalian expression vector for DACH1 or with a control vector and GFP. FIGS. 9A and 9B show the sensitivity to increasing doses of CC115, a dual inhibitor of DNA-dependent protein kinase (DNA-PK) and mammalian target of rapamycin (mTOR), or VX-984, a DNA-PK inhibitor that inhibits non-homologous end joining, respectively. The assessment of sensitivity to CC115 (see FIG. 9A) or VX-984 (see FIG. 9B) after 72 hours. The data is shown as mean±SEM for 3 separate experiments (9 replicate data points).

Example 6

Figure 10:
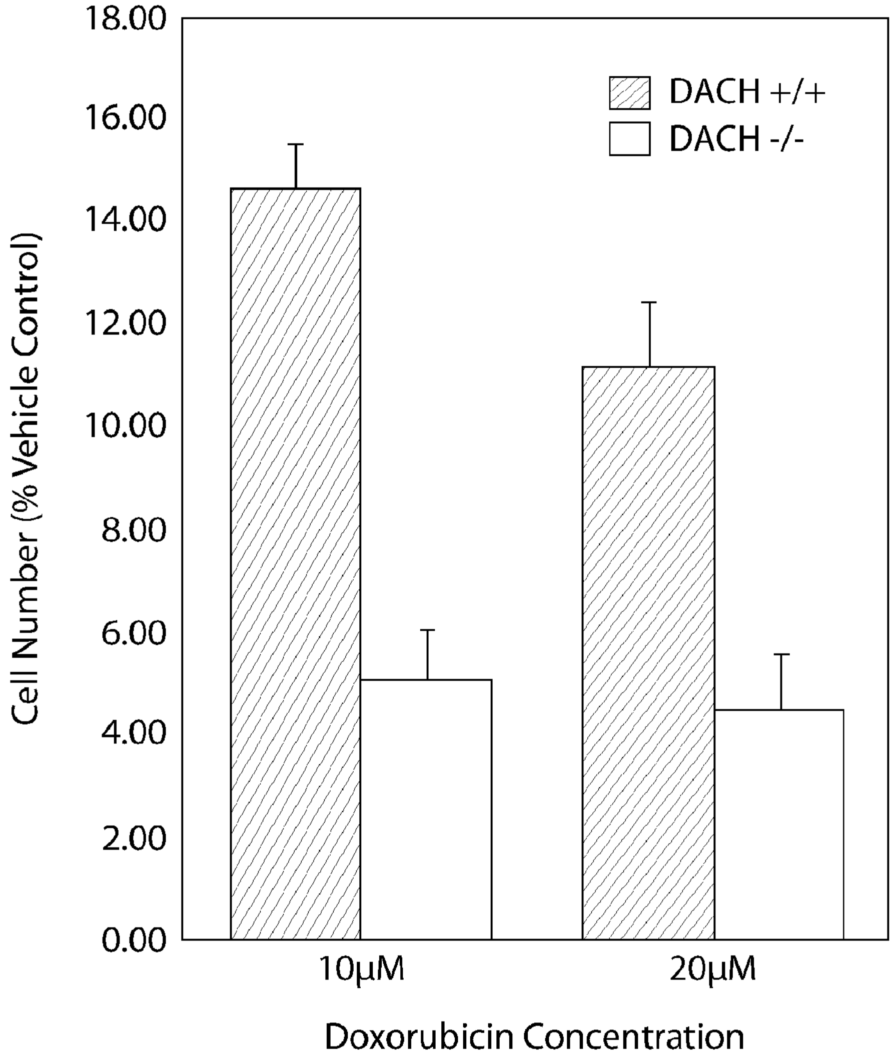
FIG. 10 is a graph showing DACH1 deficiency was determined to effect sensitivity to DNA damaging agents according to aspects of the invention.

DACH1 deficiency was determined to effect sensitivity to DNA damaging agents (e.g., doxorubicin). DACH1$^{+/+}$ and DACH1$^{-/-}$ 3T3 cells were treated for 72 h with increasing doses of doxorubicin, a DNA damaging agent. The data is shown in FIG. 10 as mean±SEM for 4 separate experiments (12 replicate datapoints).

Example 7

Figure 11A:
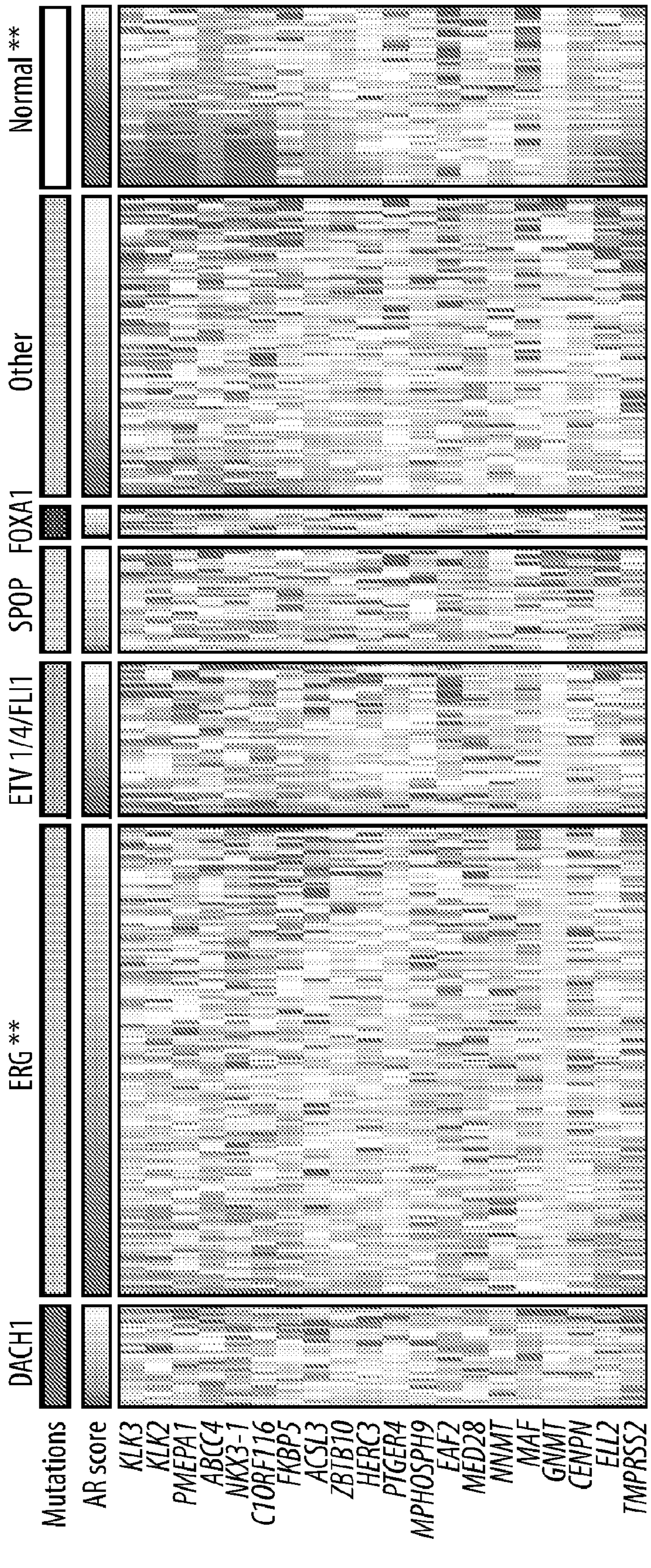
FIGS. 11A-11D are graphs showing the interrogation of a principal component analysis (PCa) gene expression database in accordance with aspects of the invention.
Figure 11B:
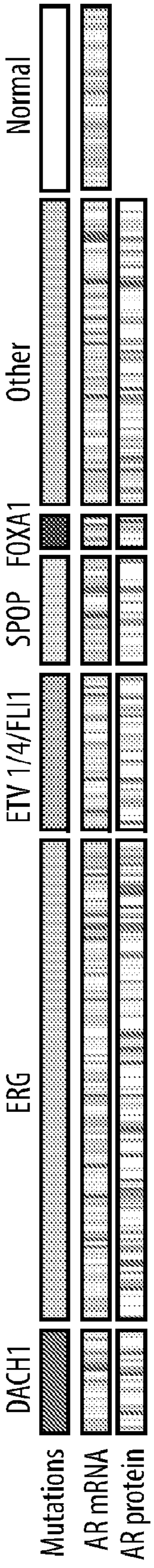
Figure 11C:
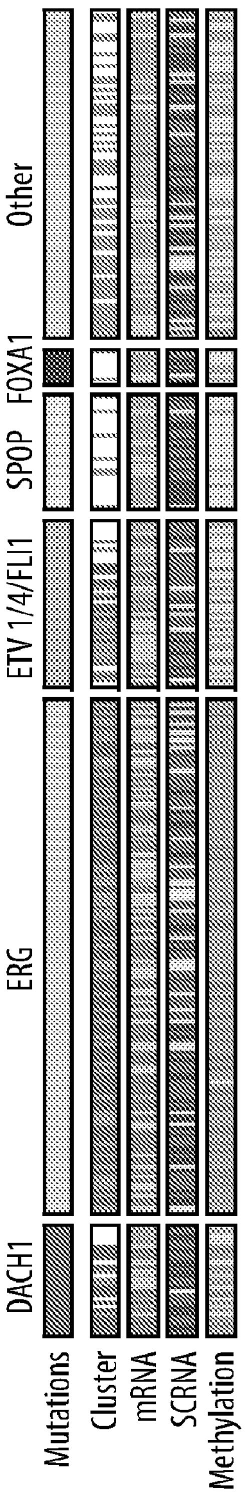
Figure 11D:
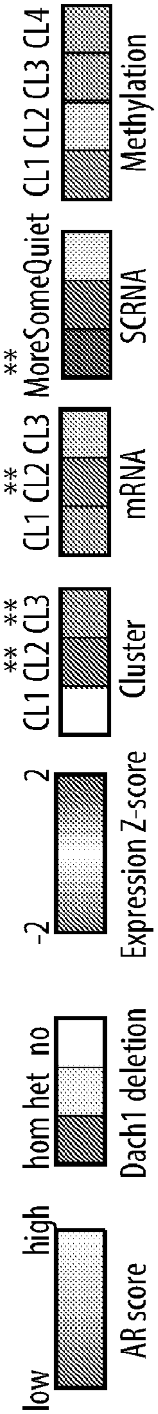

A PCa gene expression database was interrogated using previously assigned candidate genetic drivers as ERG, ETV1/ETV4/FLI1, SPOP, FOXA1 and unknown (see FIG. 11A). DACH1 genetic deletions (29/333) were assigned to this cohort and shown as an additional subtype (see FIG. 11B). The diversity of androgen receptor (AR) activity, inferred by the induction of AR target genes was increased in DACH1 deletion PCa as compared with normal ($p=2\times10^{-5}$ by t-test) and ERG1 mutation groups (p=0.003 by t-test) (see FIGS. 11C and 11D). DACH1 deep deletions are relatively enriched for icluster 2,3. Icluster refers to integrative clustering of tumor gene expression. The data was obtained using mRNA cluster 2 (p=0.0003), SCRNA (“more” somatic copy-number alteration, p=0.0004), but not for DNA methylation.

Example 8

Figure 12A:
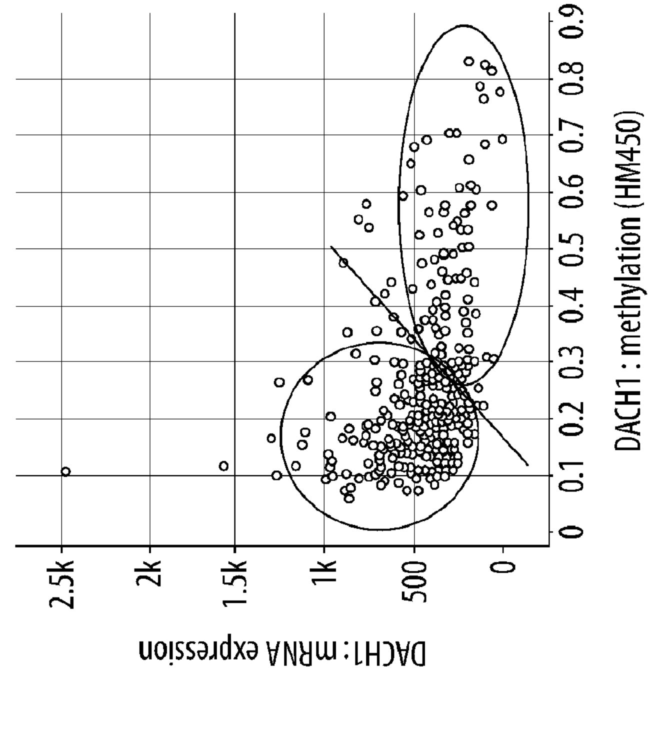
FIG. 12A is a graph of DACH1 mRNA expression vs. DACH1 methylation according to aspects of the invention.
Figure 12B:
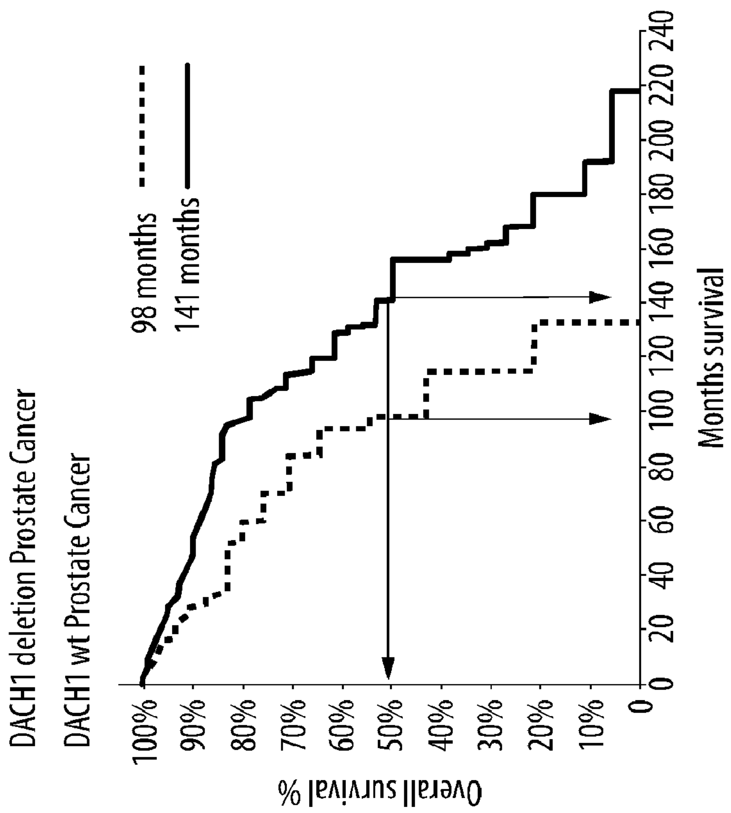
FIG. 12B is a graph showing expression of DACH1 correlates with reduced overall survival in accordance with aspects of the invention.

The DACH1 gene can be deleted in human prostate cancers. As seen in FIG. 12A, DACH1 mRNA expression vs. DACH1 methylation illustrates significant correlation between methylation of the DACH1 promoter and reduced mRNA in prostate cancer. As seen in FIG. 12B, the expression of DACH1 correlates with reduced overall survival (N=1,476 patients), wherein patients with deep DACH1 deletions showed reduced overall survival (log rank, P<4.8 $e^{-4}$).

Example 9

Figure 13A:
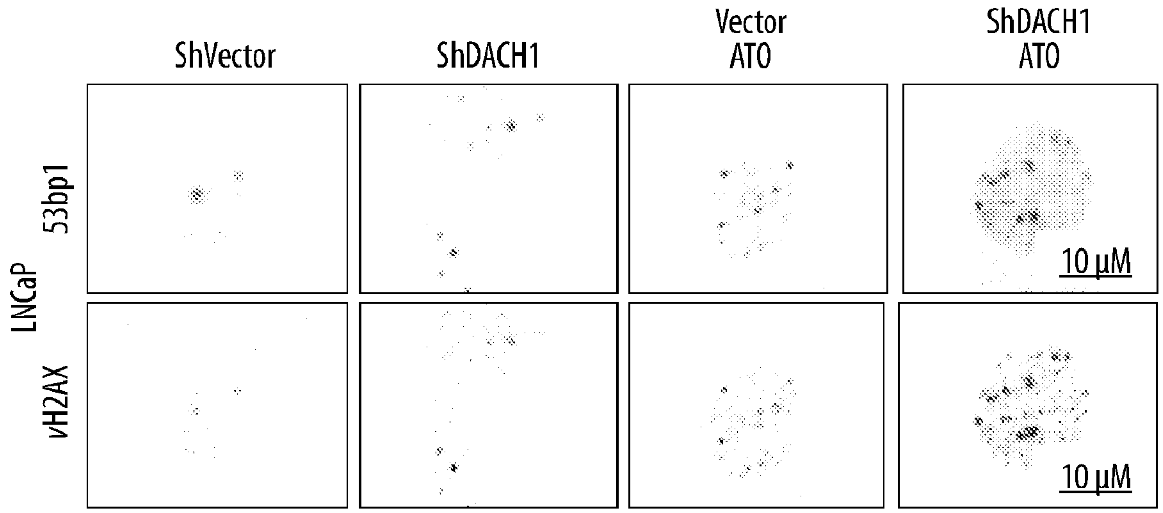
FIG. 13A is images of LNCaP cells stably transduced with control vector or shDACH1 and treated with ATO according to aspects of the invention.
Figure 13B:
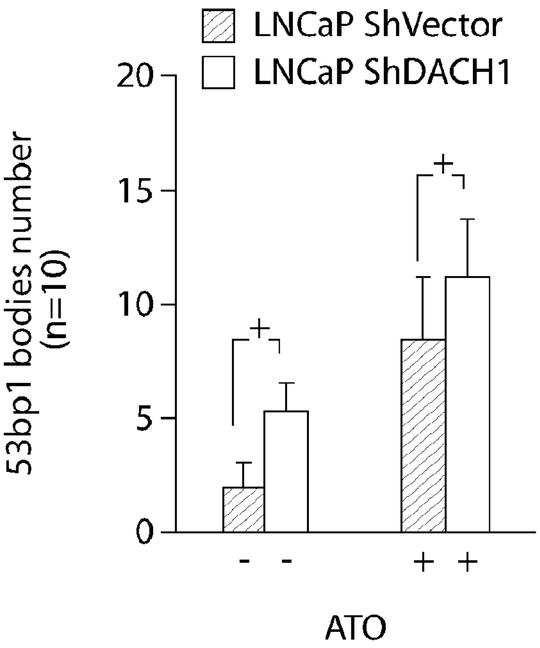
FIG. 13B is a graph of LNCaP cells stably transduced with control vector or shDACH1 and treated with ATO according to aspects of the invention.

DACH1 was determined to enhance non-homologous end joining (NHEJ). LNCaP cells stably transduced with control vector or shDACH1 were treated with ATO (1 mm) and immunofluorescence for 53BP1 or gH2AX (see FIGS. 13A and 13B). Quantitation is shown in FIGS. 13A and 13B as mean±SEM for N=10 separate cells.

Example 10

Figure 14A:
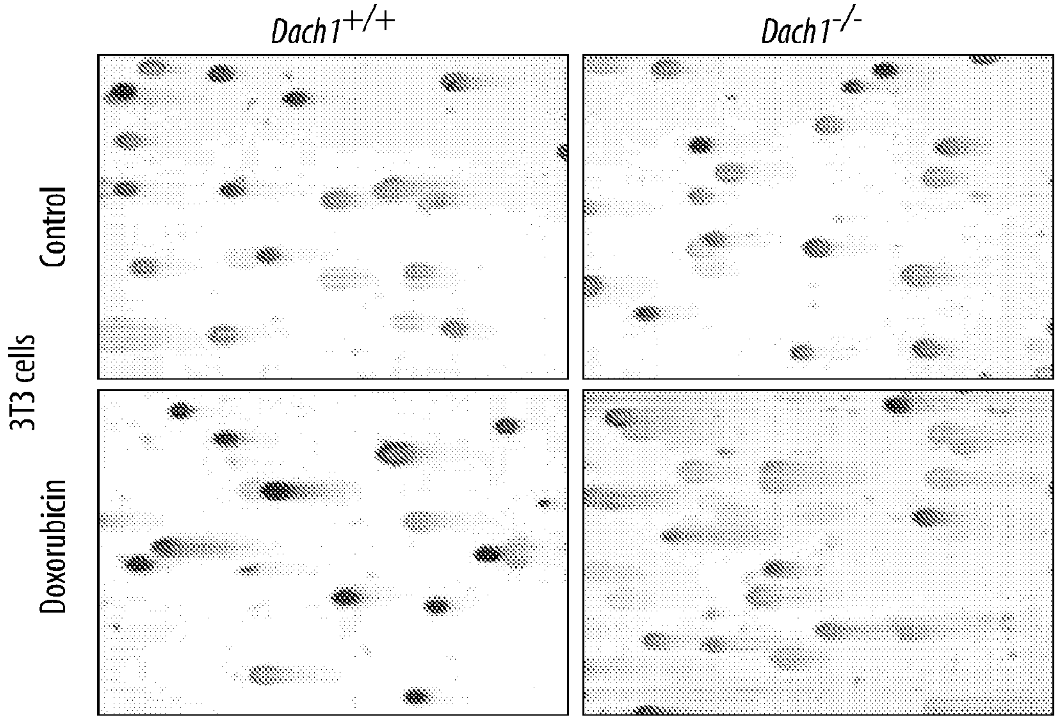
FIG. 14A is an image of a comet assay prepared for assessing DACH1 on DNA repair in accordance with aspects of the invention.
Figure 14B:
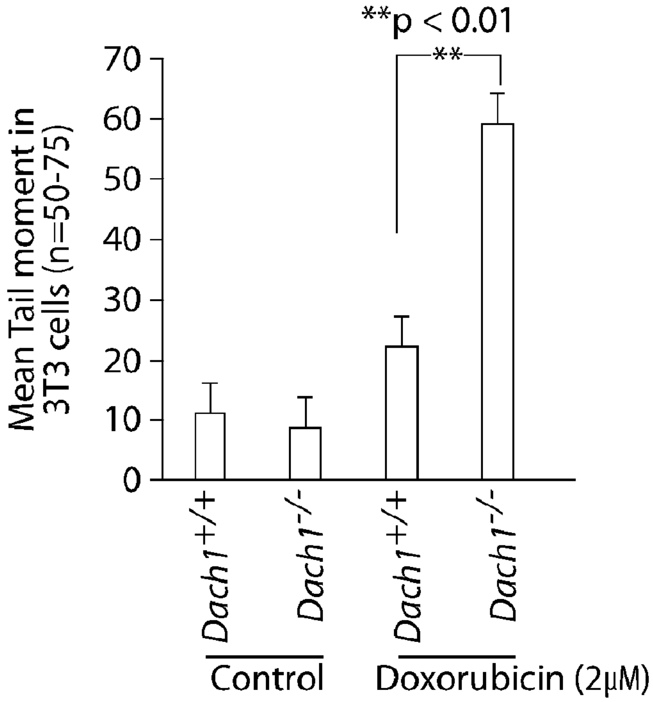
FIG. 14B is a graph the effect of doxorubicin on 3T3 cells having the DACH1 gene or a deletion of the DACH1 gene according to aspects of the invention.

The effect of DACH1 on DNA repair was assessed. The comet assay (see FIG. 14A) was conducted as a single cell DNA damage assay at neutral pH. Neutral pH comet assay detects mainly DNA double strand breaks (DSBs). $DACH1^{+/+}$ and $DACH1^{-/-}$ 3T3 cells were treated with 2 μM doxorubicin for 18 hrs. The scale bar in FIG. 14B is 100 μm with data shown as mean±SEM from 5 separate experiments.

Example 11

Figure 15A:
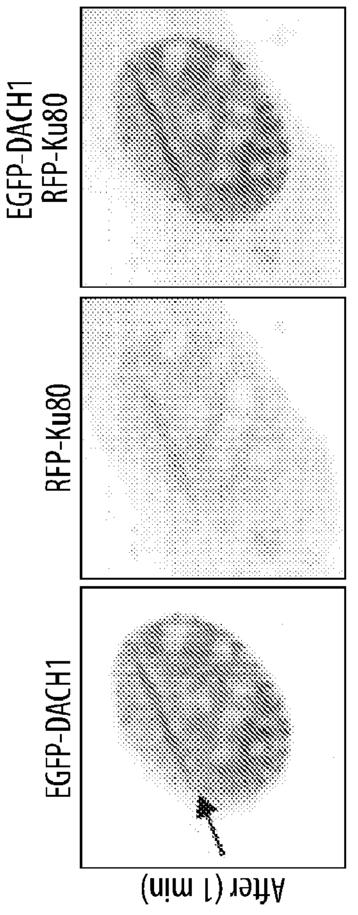
FIG. 15A provides images of cells transfected with GFP or GFP-tagged DACH1 and red fluorescent protein (RFP)-tagged Ku80 expression vectors and treated with laser microirradiation to induce DSBs sites in accordance with aspects of the invention.
Figure 15B:
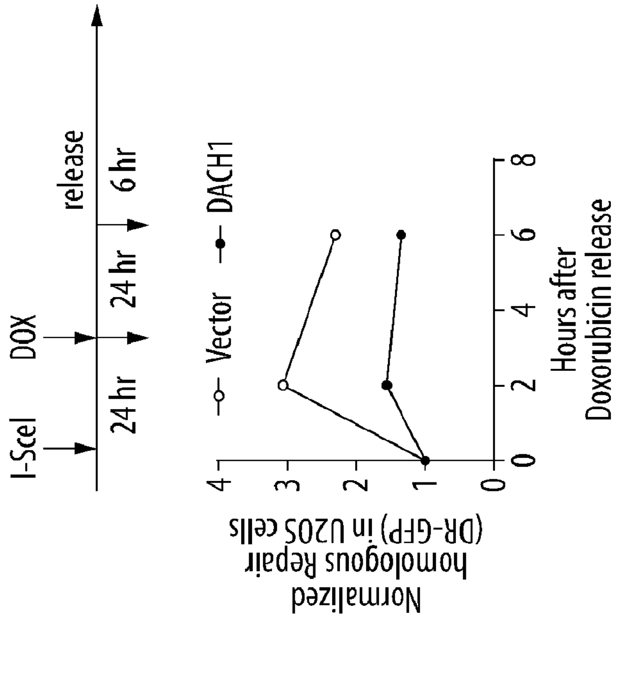
FIGS. 15B and 15C show graphs of assays for homologous repair (EJ2-GFP) and homologous repair (DR-GFP) were conducted in DACH1$^{-/-}$ 3T3 cells or DACH1 rescued DACH1$^{-/-}$ 3T3 cells according to aspects of the invention.
Figure 15C:
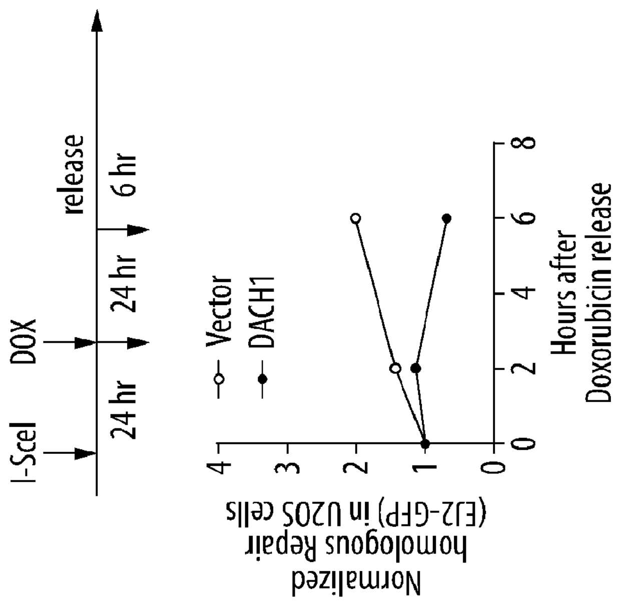

DACH1 was determined to enhance recruitment of DNA repair factors. Co-accumulation of DACH1 and Ku-80 at laser microirradiation-induced DSBs sites. $DACH1^{-/-}$ 3T3 cells were transfected with GFP or GFP-tagged DACH1 and red fluorescent protein (RFP)-tagged Ku80 expression vectors and treated with laser microirradiation to induce DSBs 24 h after transfection before and after irradiation. Accumulation of the transfected proteins was indicated by GFP (green) or RFP (red) fluorescence at laser-irradiated sites. Yellow arrowheads indicate direction of laser irradiation. Co-accumulation was visualized in yellow merged images (see FIG. 15A). Reporter assays for homologous repair (EJ2-GFP) and homologous repair (DR-GFP) were conducted in $DACH1^{-/-}$ 3T3 cells or DACH1 rescued $DACH1^{-/-}$ 3T3 cells. The 3T3 cells were treated for 24 h with doxorubicin ("Dox") and DNA repair activity was assessed at the time points indicated after removal of Dox (see FIGS. 15B and 15C).

Example 12

Figure 16A:
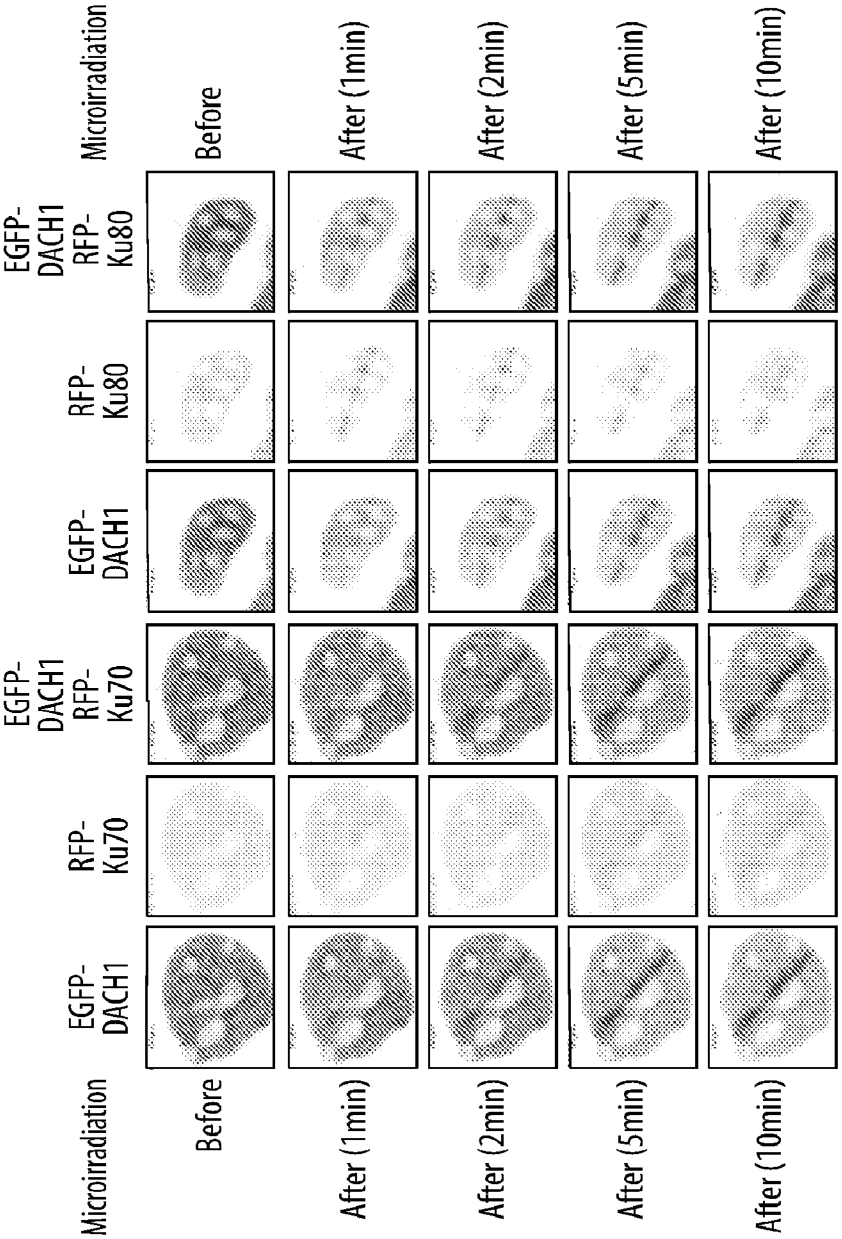
FIGS. 16A and 16B are images of 3T3 cells that were transfected with GFP-tagged DACH1 and red fluorescent protein (RFP)-tagged Ku80 or Ku70 expression vectors in accordance with aspects of the invention.
Figure 16B:
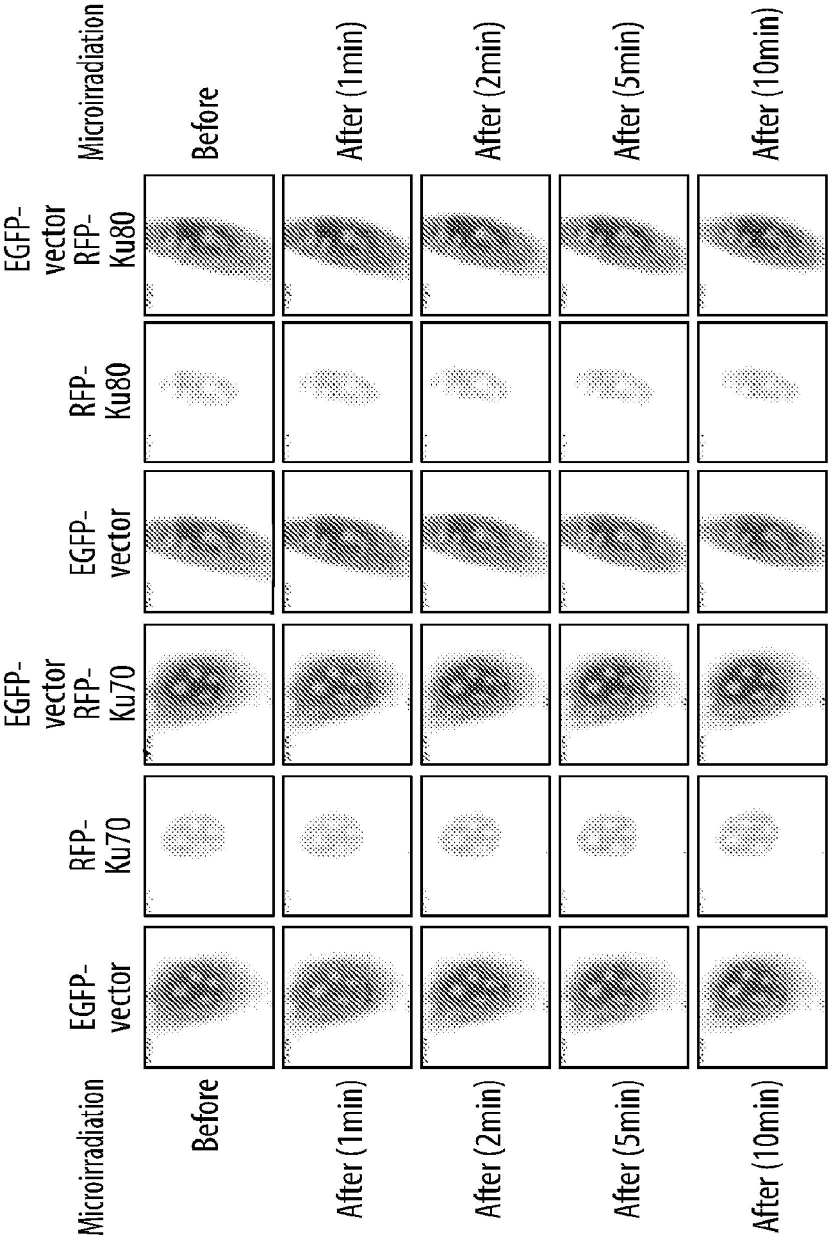

$DACH1^{-/-}$ 3T3 cells were transfected with GFP-tagged DACH1 and red fluorescent protein (RFP)-tagged Ku80 or Ku70 expression vectors. $DACH1^{-/-}$ 3T3 cells were then treated with laser microirradiation to induce DSBs 24 h after transfection before and after irradiation. Accumulation of the transfected proteins was indicated by GFP (green) or RFP (red) fluorescence at laser-irradiated sites. Yellow arrowheads indicate direction of laser irradiation. Co-accumulation was visualized in yellow merged images. Cells were transfected with GFP and either Ku70 or Ku80 expression vectors as described above. In the absence of co-expressed DACH1, neither Ku70 nor Ku80 were recruited to the site of DNA damage in $DACH1^{-/-}$ 3T3 cells. The co-accumulation of DACH1 and Ku-80 at laser microirradiation-induced DSBs sites indicates that DACH1 enhances recruitment of DNA repair factors (See FIGS. 16A and 16B).

Example 13

Figure 17A:
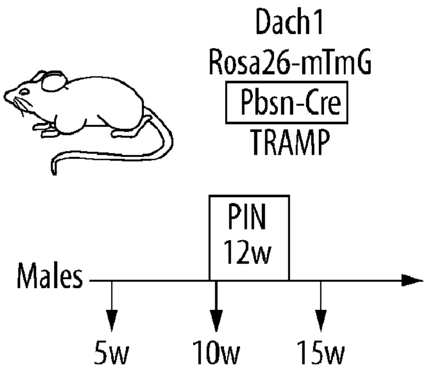
FIG. 17A is a schematic of transgenes integrated into mice according to aspects of the invention.
Figure 17B:
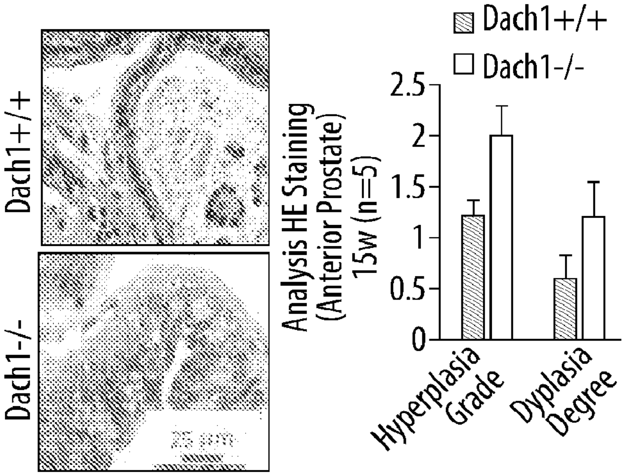
FIG. 17B is a non-limiting representative immunohistochemistry for DACH1 staining in sections of prostate tissue in accordance with aspects of the invention.
Figure 17C:
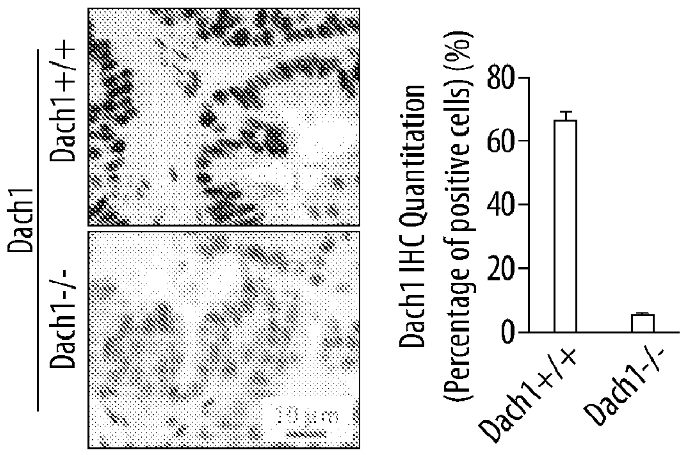
FIG. 17C shows quantitative histology grading of prostate (anterior lobe) of multigenic mice at 15 weeks according to aspects of the invention.
Figure 17D:
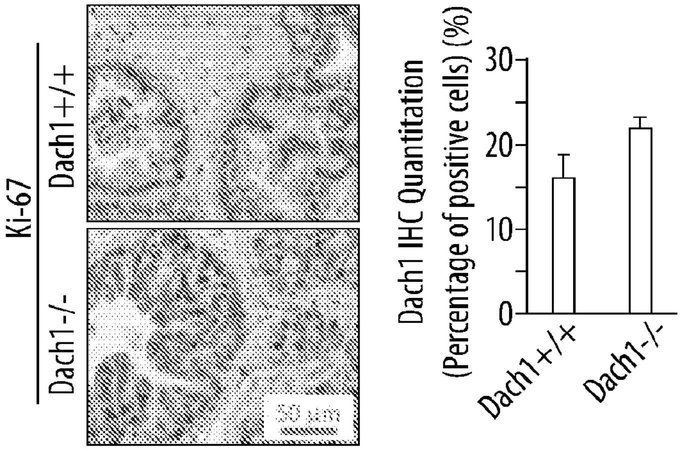
FIG. 17D shows Ki-67 staining for cell proliferation performed on sections of the prostate (anterior lobe) of multigenic mice at 15 weeks using hematoxylin as a nuclear counterstain in accordance with aspects of the invention.
Figure 17E:
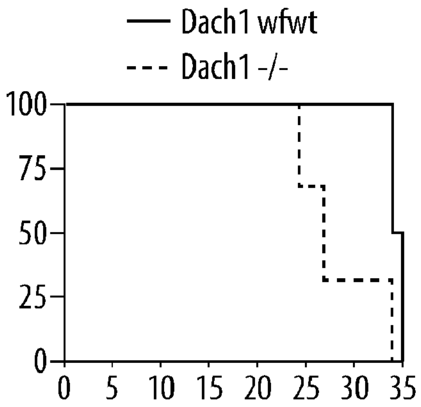
FIG. 17E is a graph indicating that Meier survival curves suggest DACH1 deletion leads to earlier onset prostate cancer in transgenic mice.

Prostate specific DACH1 gene deletion promotes prostate hyperplasia and dysplasia in OncoMice (15 weeks). FIG. 17A is a schematic representation of transgenes integrated into mice. A representative immunohistochemistry for DACH1 staining in sections of prostate tissue in FIG. 17B. Blinded quantitative histology grading of prostate (anterior lobe) of multigenic mice at 15 weeks is shown in FIG. 17C. H&E staining demonstrates the presence of a focal atypical intraductal proliferation in $DACH1^{-/-}$ prostate, compatible with prostatic intraepithelial neoplasia (PIN). As seen in FIG. 17D, Ki-67 staining for cell proliferation was performed on sections from the prostate (anterior lobe) of multigenic mice at 15 weeks using hematoxylin as a nuclear counterstain (blue). The scale bar are shown for each analysis is 10, 25 or 50 μm. A t-test student was performed to all comparison. All pictures in FIGS. 17B-17C are representative of each cohort of mice with data shown as mean±SEM, (n=3 separate mice). As seen in FIG. 17E, a Kaplan Meier survival curves suggest DACH1 deletion leads to earlier onset prostate cancer when compared to control (Wt) mice Data are from cohort of transgenic mice.

Example 14

Figures 18A, 18B:
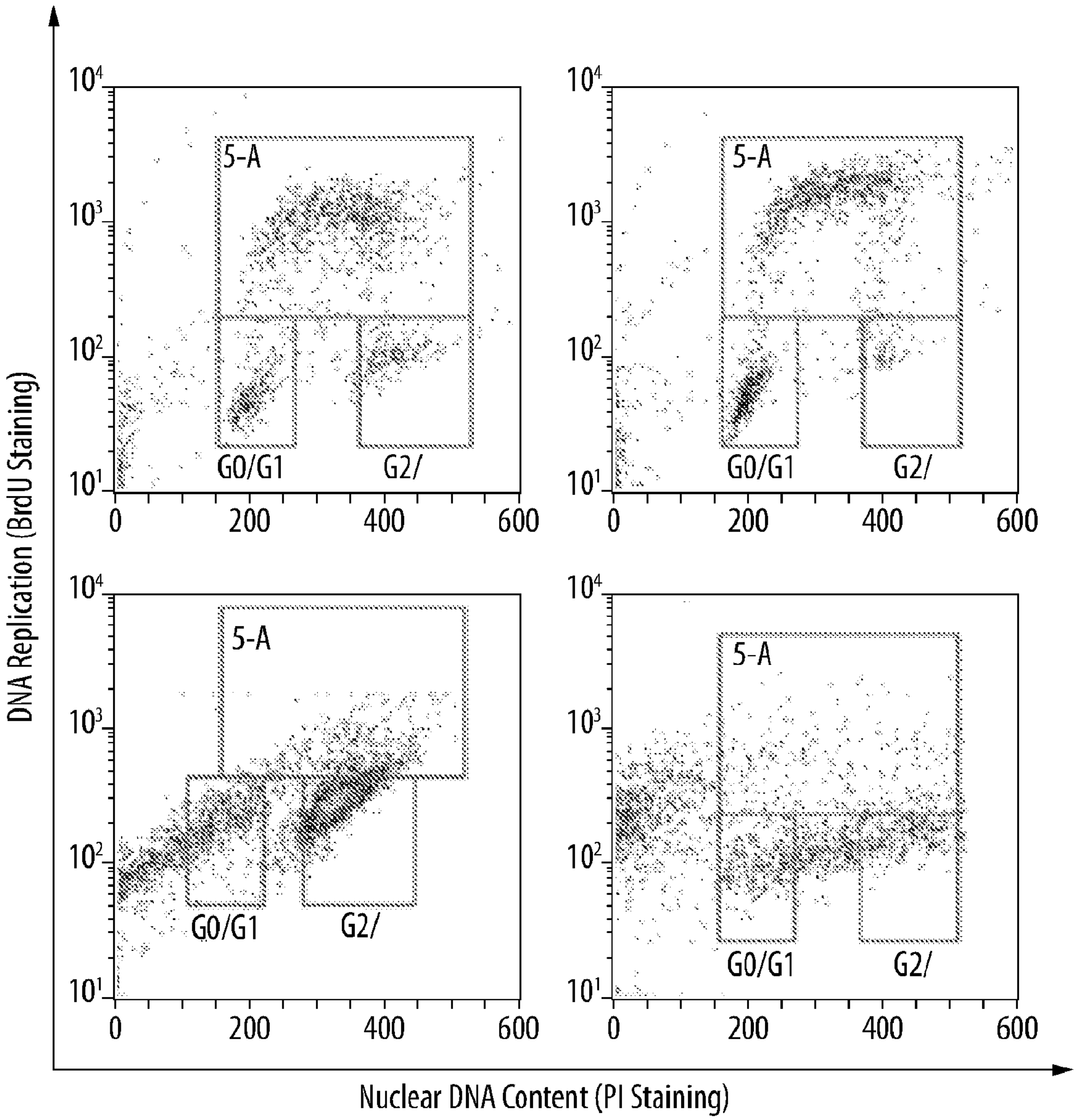
FIG. 18A is graph showing $DACH1^{+/+}$ and $DACH1^{-/-}$ 3T3 cells treated with a small molecule inhibitor of the tyrosine kinase WEE1, or with DMSO, as the control, according to aspects of the invention.
FIG. 18B is a table of the compositions administered to the 3T3 cells of FIG. 18A.
Figure 19A:
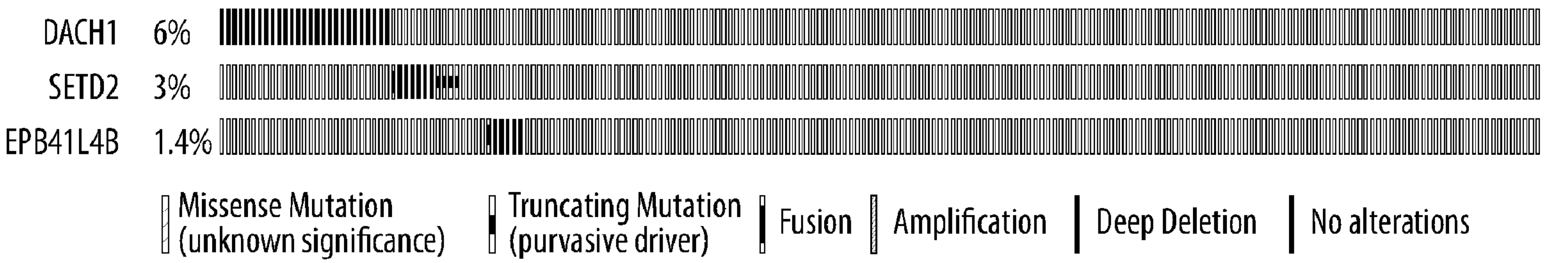
FIGS. 19A-19E are graphs of S-phase population in 3T3 cells showing an increase in $DACH1^{-/-}$ 3T3 cells compared to Wt ($DACH1^{+/+}$) controls in accordance with aspects of the invention.
Figure 19B:
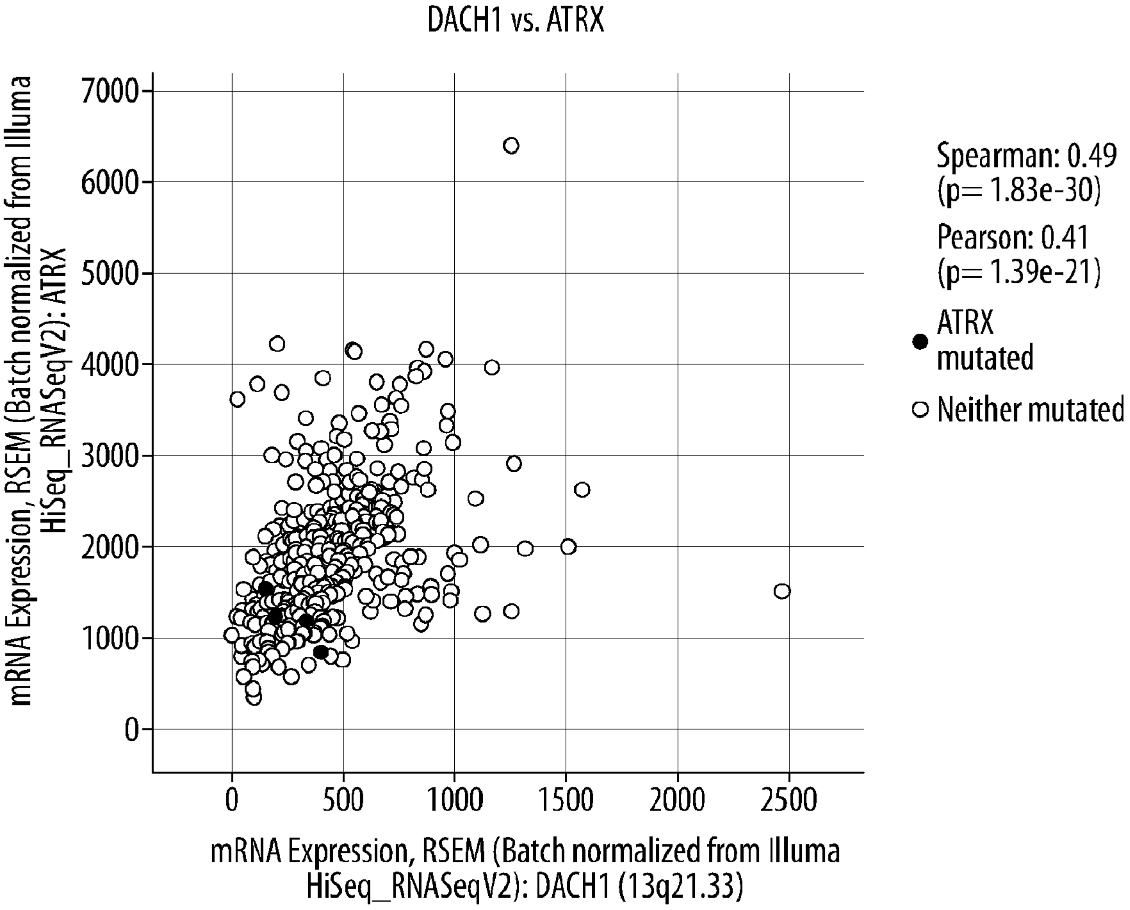
Figure 19C:
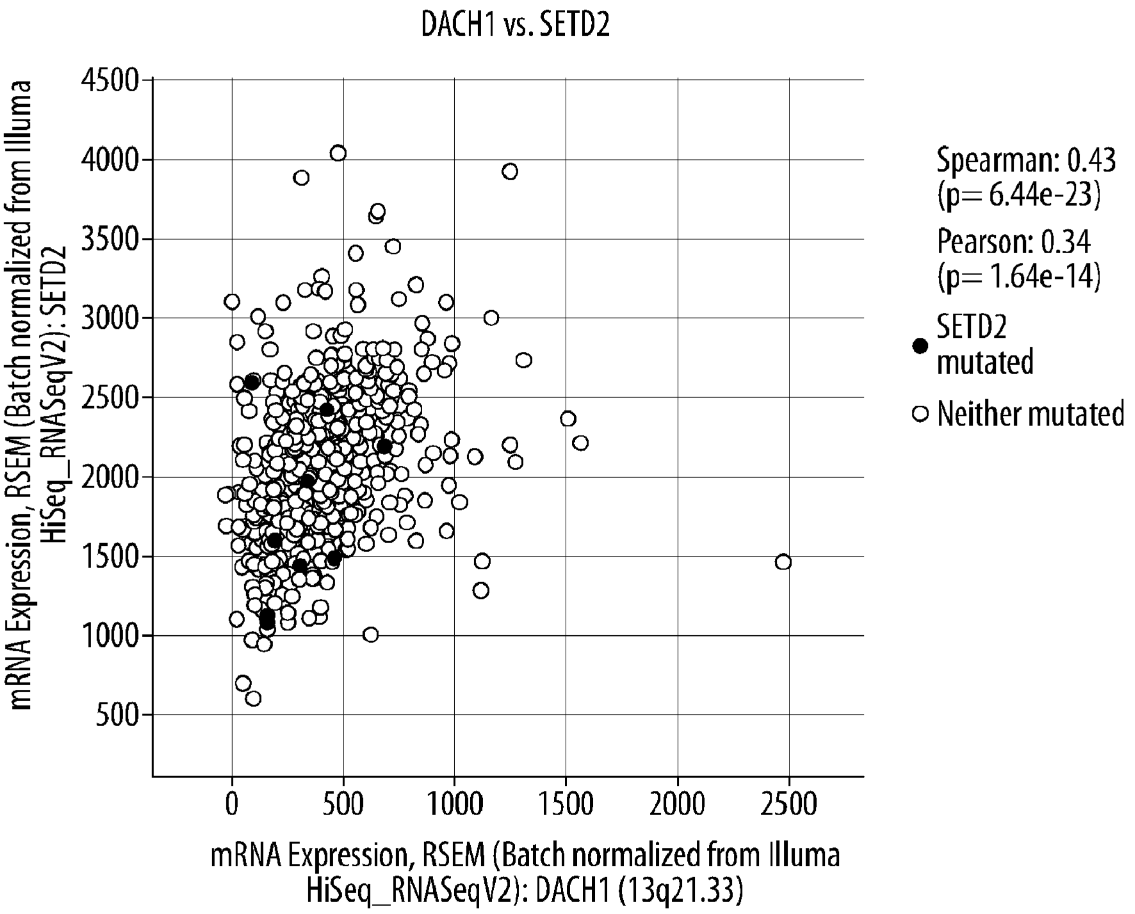
Figure 19D:
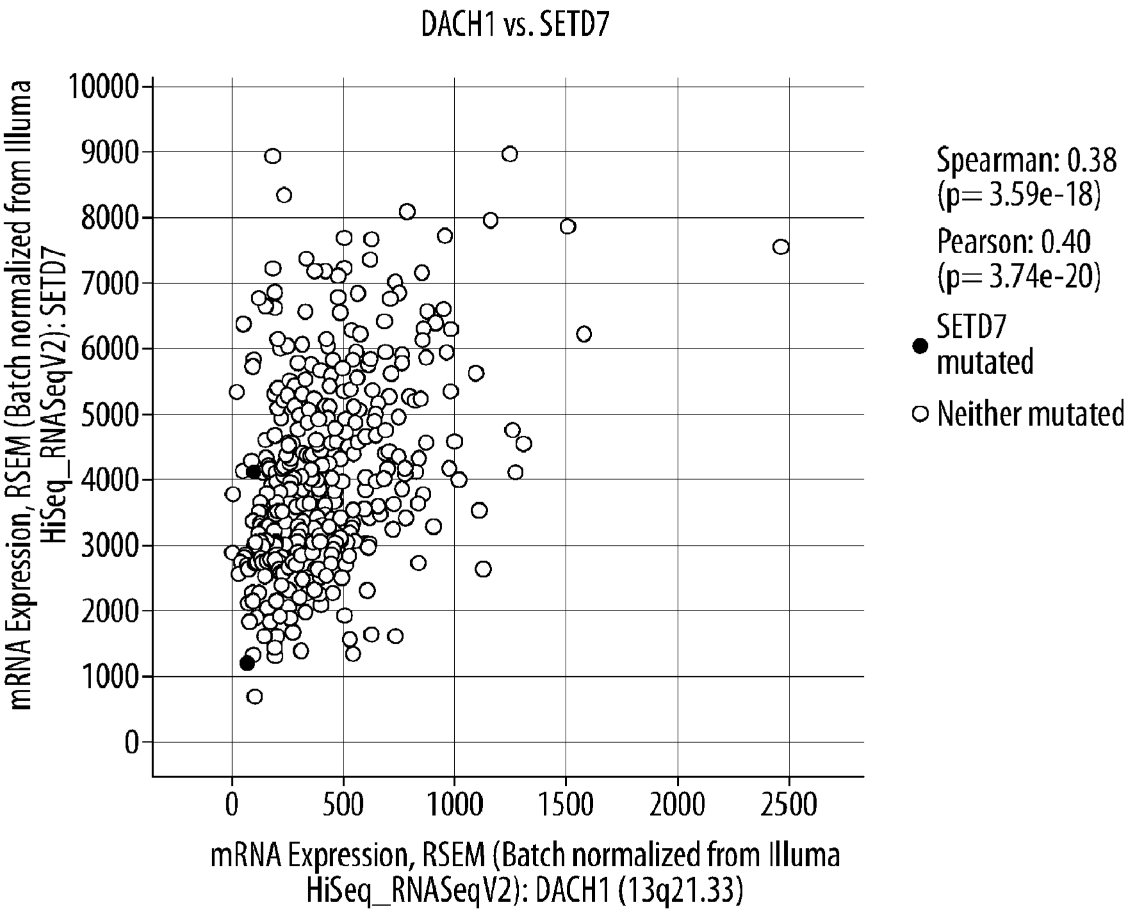
Figure 19E:
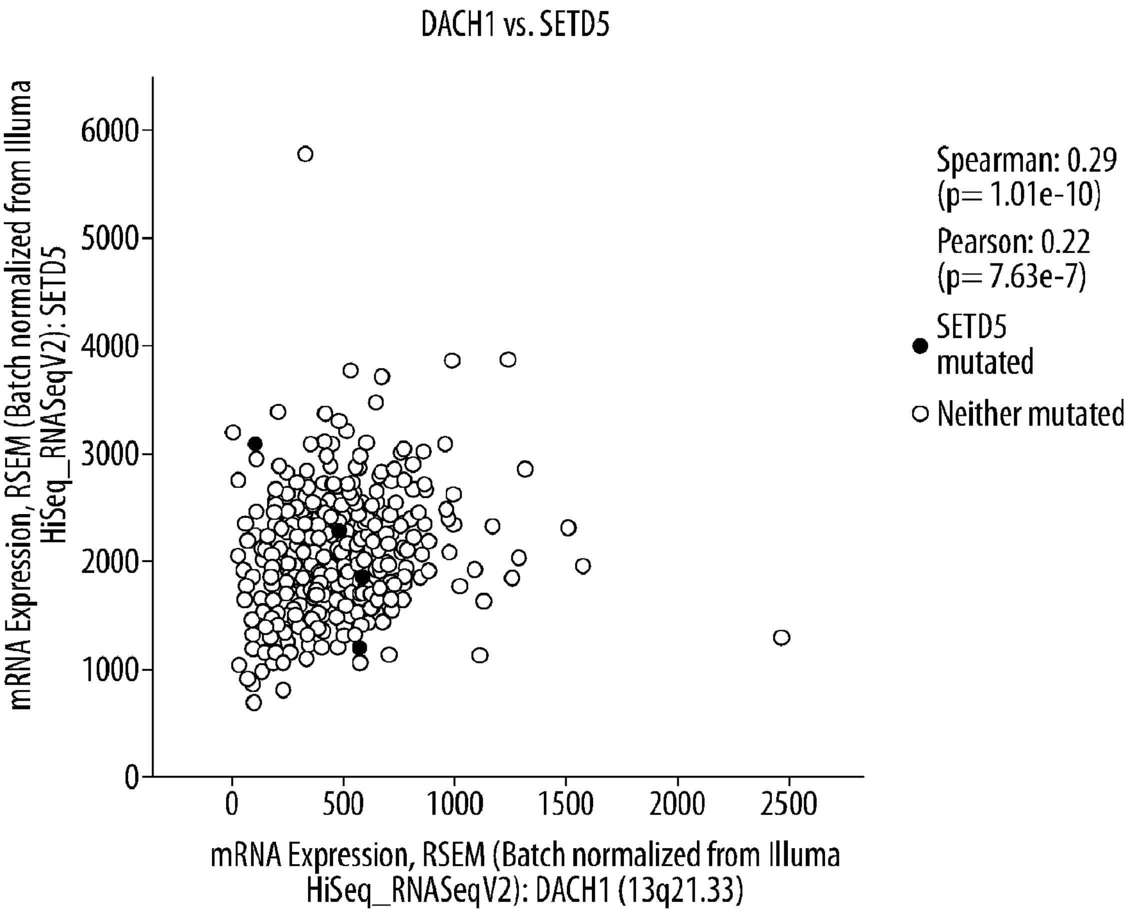

DACH1 deficiency was determined to promote accumulation of non-proliferative S-phase cells by WEE1 kinase inhibitors. $DACH1^{+/+}$ and $DACH1^{-/-}$ 3T3 cells were treated for 24 h with Adavosertib at 10 μM, a small molecule inhibitor of the tyrosine kinase WEE1, or with DMSO, as the control (see FIGS. 18A and 18B). Prior to harvest, the 3T3 cells were pulsed with 20 μM BrdU for 30 min at a temperature of 37° C. to enable detection of cells with active DNA replication. After harvesting the 3T3 cells, the 3T3 cells were stained with propidium iodide (DNA content) and an anti-BrdU antibody (Abcam). 2 color analysis of the resulting cell suspension by flow cytometry revealed that the $DACH1^{+/+}$ and $DACH1^{-/-}$ 3T3 cells had similar cell cycle kinetics under control conditions. However, upon inhibition of WEE1 kinase, the $DACH1^{-/-}$ cells failed to incorporate the BrdU consistent with the induction of mitotic collapse. Representative FACS plots are shown (see FIGS. 19A-19E). Quantitation of the non-proliferating S-phase population in labelled 3T3 cells showing an increase in $DACH1^{-/-}$ 3T3 cells compared to Wt ($DACH1^{+/+}$) controls (38.3% vs 13.8%). Data is shown as mean±SEM for 4 separate experiments.

Example 15

Figure 20:
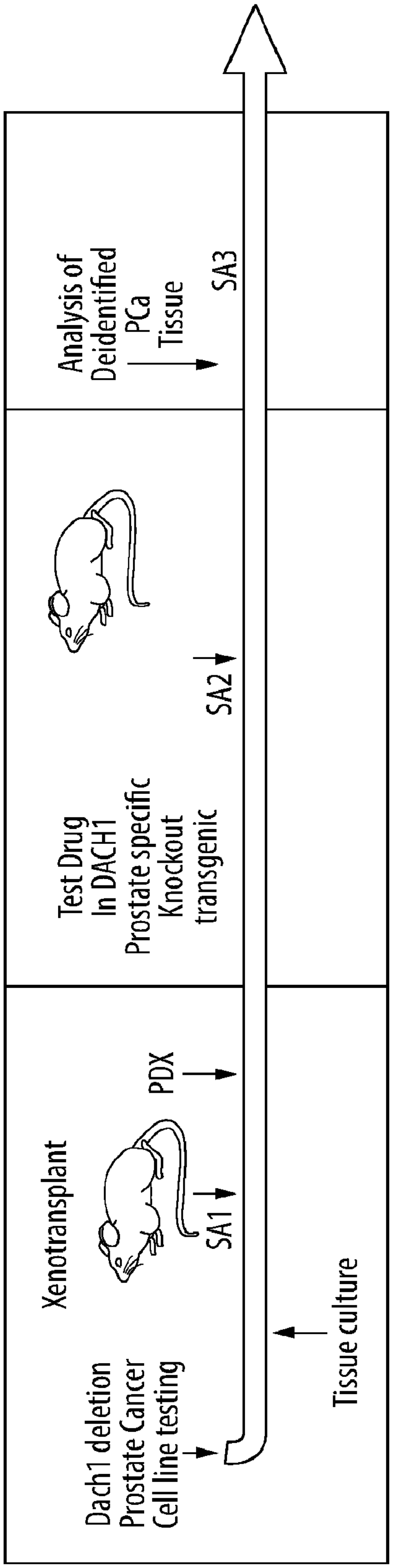
FIG. 20 is a schematic representation for analyzing prostate cancer tissue using transgenic mice according to aspects of the invention.
Figure 21A:
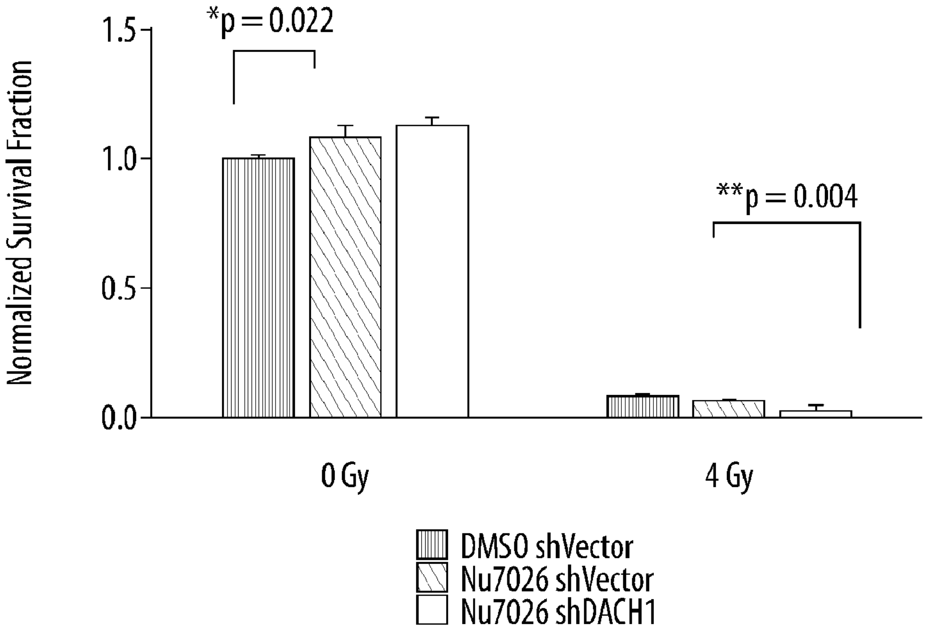
FIGS. 21A and 21B are graphs showing that DACH1 knockdown enhances the cell killing by DNA PK inhibitors and enhance the effect of radiation with DNA-PK inhibitors—in colony forming assays and in cell proliferation assays in accordance with aspects of the invention.
Figure 21B:
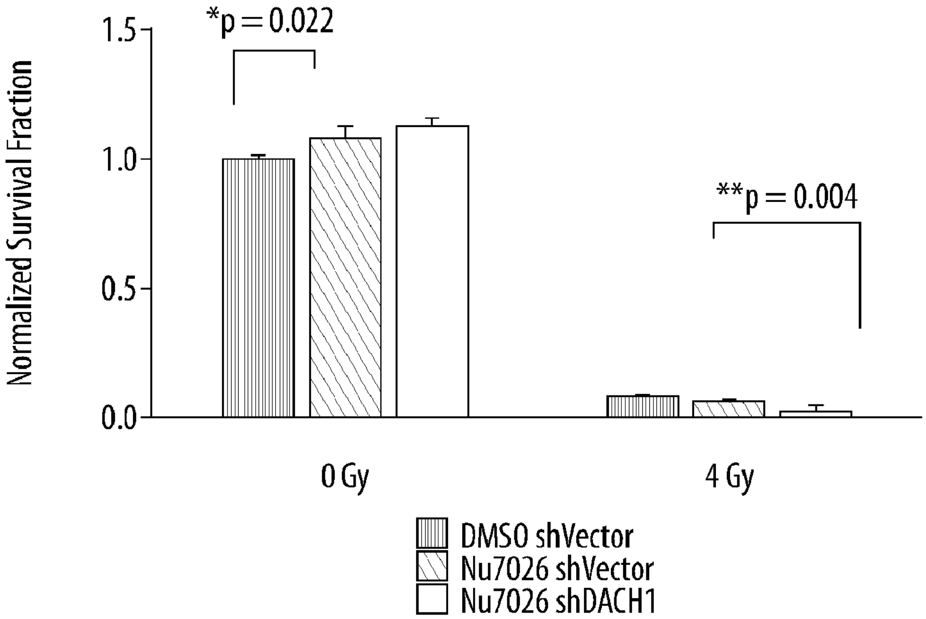
Figure 22A:
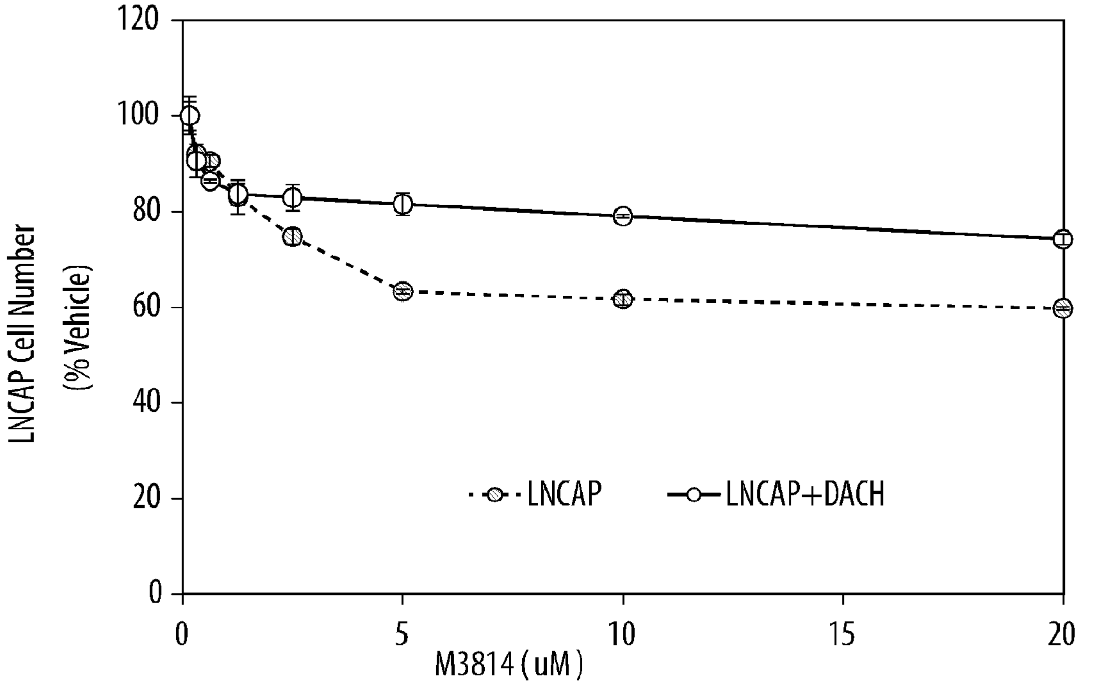
FIGS. 22A and 22B are graphs showing the effect of DNA-PK inhibitor, M3814, on LNCaP cells and DU145 cells having the presence or deletion of DACH1, respectively, according to aspects of the invention.
Figure 22B:
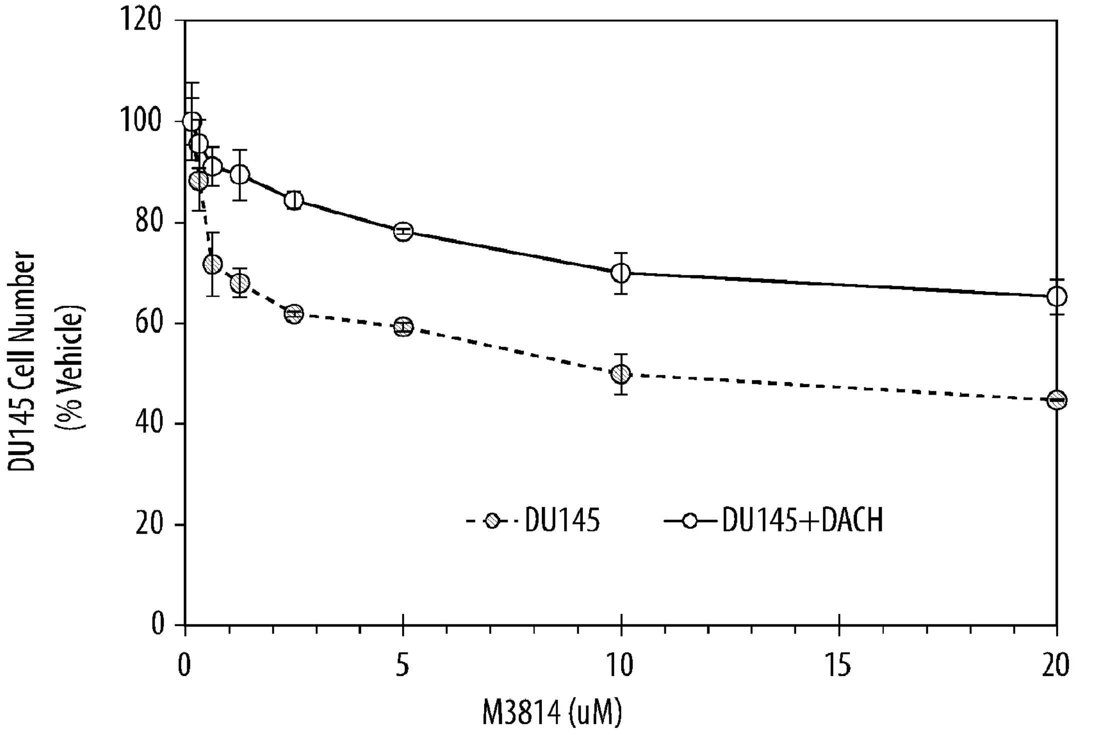

Diagnostics will deploy a model system of PCa in which DACH1 has been genetically deleted in the prostate of a transgenic mouse (see FIG. 20). Prostate cancer cells from the transgenic mice will be tested to assess DACH1 deleted PCa cells for vulnerability to PCa therapeutics. To potentially produce aggressive prostate cancer, a genomic deletion at 13q21 will be induced in the transgenic mice.

Further, a genetically engineered mouse models (GEMM) may also be produced. Photo-uncaging of transgenic PCa cells will be used to induce Cre recombinase and enable us to mark DACH1+/+ vs. DACH1−/− sibling cells with a transgenic red-green color switch.

Additionally, analysis of human PCa tissue arrays will be evaluated to determine the potential predictive value of DACH1 gene deletion in response to specific PCa therapeutics. For example, novel isogenic oncogene specific PCa cell lines will prospectively be developed, which resemble human PCa. These lines should, in theory, reliably metastasize to bone, lung and brain in immune-competent FVB mice. In a study of 74,826 patients PCa metastasized to bones (84%), lymph nodes (11%), thorax (9%), and brain (12%). Thus, isogenic oncogene specific PCa cell lines may be used to capture the full spectrum of metastasis translational studies on DACH1 and PCa metastasis.

The human PCa cells may be used to follow prostate epithelial cell fate regulated by DACH1 and potentially determine sister cell function dependent upon DACH1 gene deletion.

Example 16

$DACH1^{-/-}$ 3T3 cells transduced with a DACH1 expression vector were treated for 3 days with Doxorubicin and increasing doses of the TGF-b receptor type I (TGF-βRI) kinase inhibitors 20 mM LY2157299, or 1 mM LY363947, or vehicle control Data are shown as FIGS. 24A-24D. Mean±SEM for N-3 separate experiments in triplicate.

Example 17

Figure 25A:
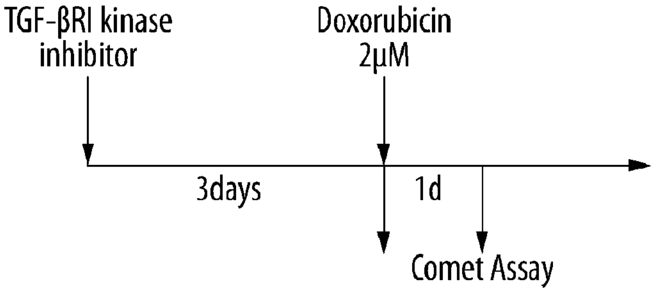
FIG. 25A is a schematic of the experimentation for assessing TGF-βRI kinase inhibitor and Doxorubicin on 3T3 cells exhibiting an abundance of DACH1 or a lack thereof in accordance with aspects of the invention.
Figure 25B:
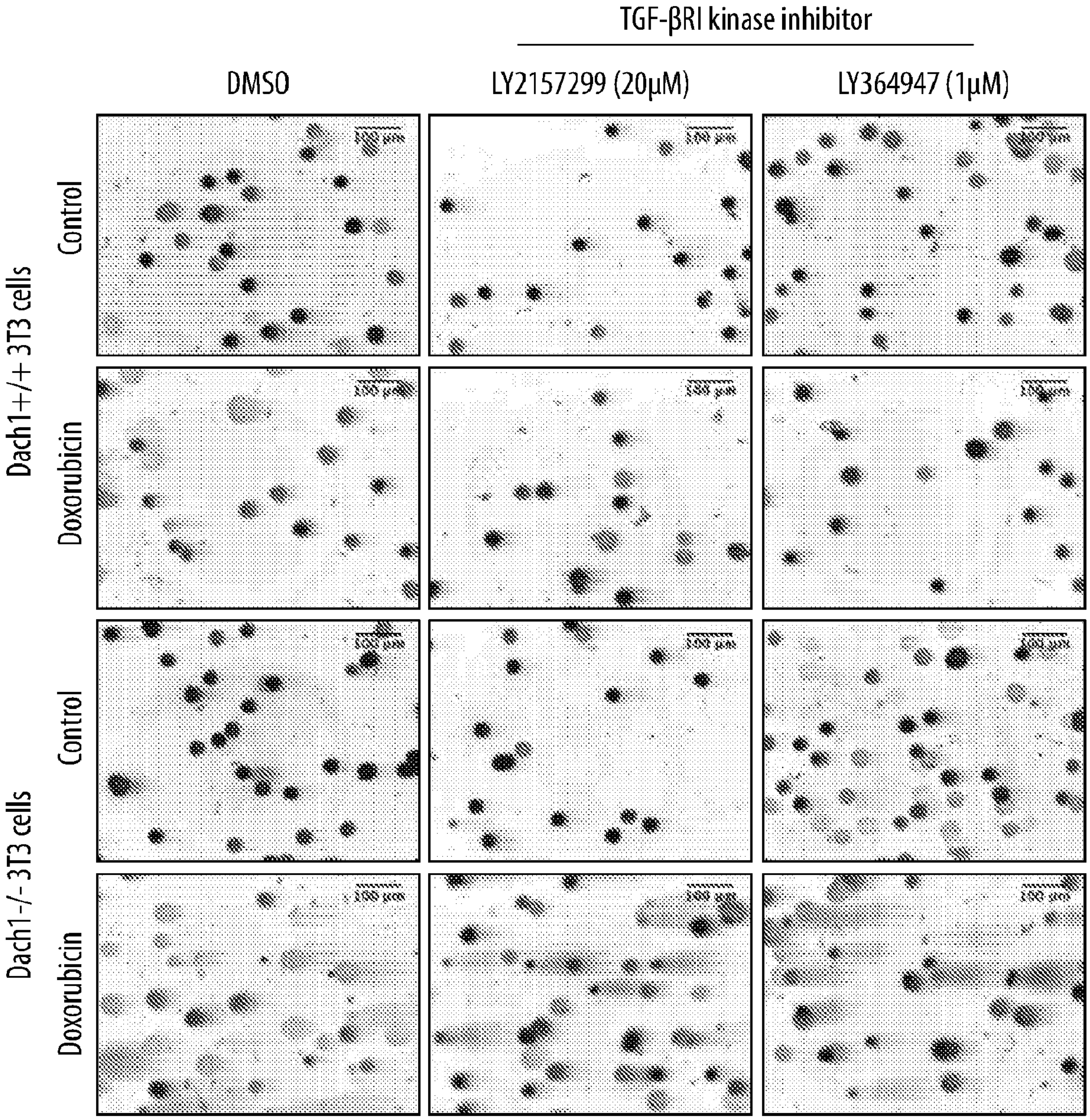
FIG. 25B is a comet assay of the 3T3 cells of FIG. 25A.
Figure 25C:
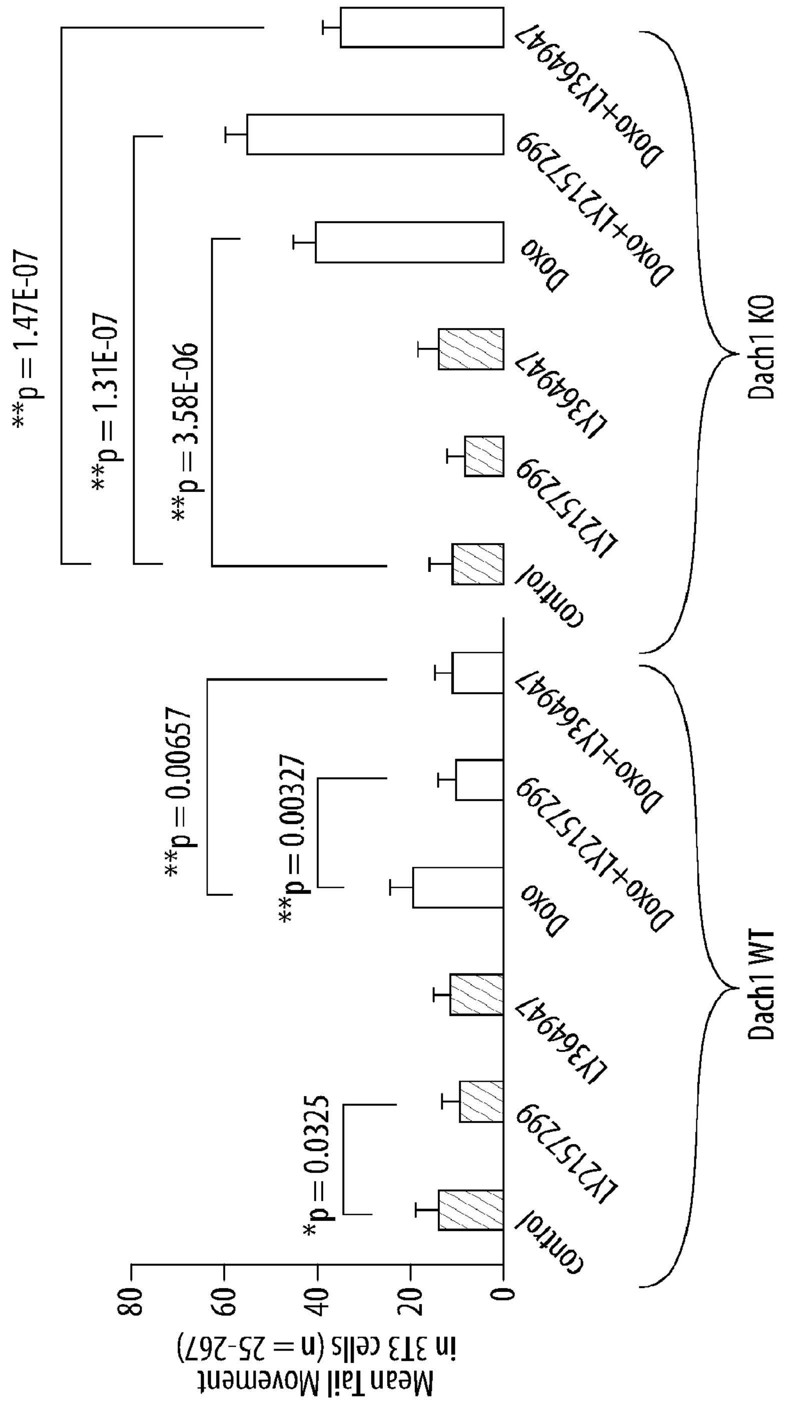
FIG. 25C is a graph of TGF-βRI kinase inhibitor and Doxorubicin on 3T3 cells exhibiting an abundance of DACH1 or a lack thereof according to aspects of the invention.
Figure 26:
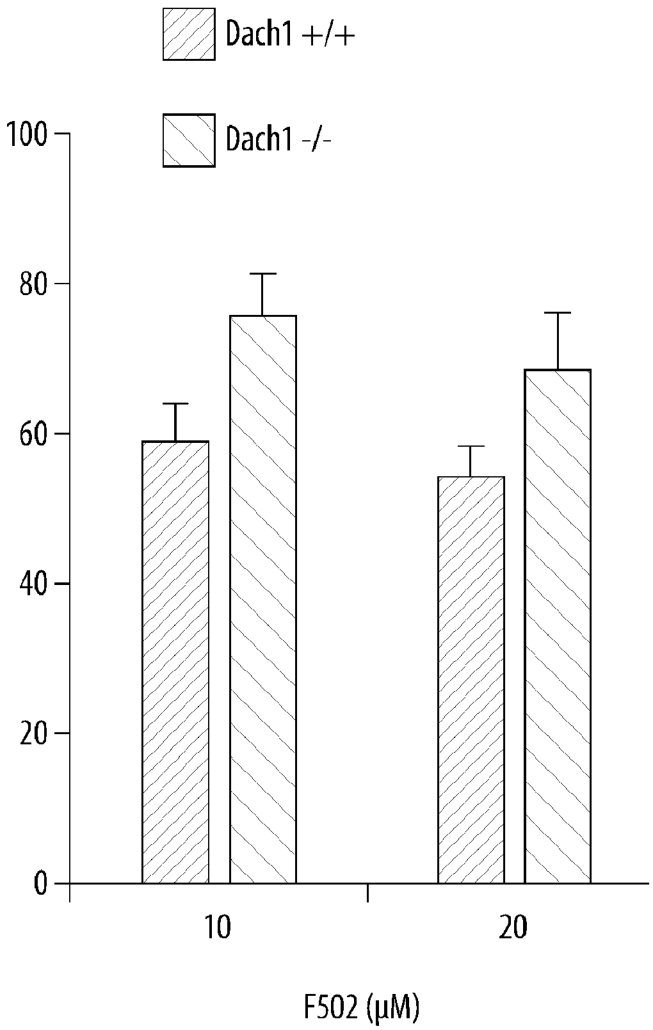
FIG. 26 is a graph of cancer cells an abundance of DACH1 or a lack thereof, which was treated with F502 in accordance with an aspect of the invention.

DACH1 WT and DACH1 KO 3T3 cells were treated with TGF-b receptor type I (TGF-βRI) kinase inhibitor 20 mM LY2157299, or 1 mM LY363947, or vehicle control DMSO for 3 days (see FIG. 25A). After treatment with 2 mM doxorubicin or control for 24 hours, the 3T3 cells were harvested and processed for neutral pH Comet assay (see FIG. 25B). Average tail moments were analyzed using OpenComet software (see FIG. 25C). Data are the mean and standard error from 125-267 cells per treatment.

What is claimed is:

1. A method for treating cancer in a subject in need thereof, the method comprising administering to the subject a therapeutically effective amount of a WEE1 inhibitor, a prodrug thereof, or a salt thereof, wherein the subject has a cancer having a deletion of a DACH1 gene or a portion thereof or not expressing or having a reduced expression of a DACH1 protein.

2. The method of claim 1, further comprising administering a DNA-PK inhibitor to the subject.

3. The method of claim 1, wherein the WEE1 inhibitor is selected from AZD1775 (MK1775); 2-allyl-1-[6-(1-hydroxy-1-methylethyl) pyridin-2-yl]-6-{[4-(4-methylpiperazin-1-yl)phenyl]aminoI-1,2-dihydro-3H-pyrazolo[3,4-d] pyrimidin-3-one; 3-(2,6-dichlorophenyl)-4-imino-7-[(2'-methyl-2',3'-dihydro-1'H-spiro[cyclopropane-1,4'-isoquinolin]-7'-yl)amino]-3,4-dihydropyrimido[4,5-d] pyrimidin-2(1H)-one, and a combination of two or more thereof.

4. The method of claim 1, wherein the cancer is selected from prostate cancer, lung cancer, or breast cancer.

5. The method of claim 1, wherein the cancer is prostate cancer.

6. The method of claim 1, wherein the subject is not administered a PARP inhibitor.

7. The method of claim 1, wherein the subject is further administered a DNA-targeted agent.

8. The method of claim 7, wherein the DNA-targeted agent comprises a DNA alkylating agent, a topoisomerase inhibitor, or a combination of two or more thereof.

9. The method of claim 7, wherein the DNA-targeted agent is selected from cisplatin, capecitabine, carboplatin, cyclophosphamide, cytarabine, daunorubicin, docetaxel, doxorubicin, 5-fluorouracil, gemcitabine, methotrexate, paclitaxel, pemetrexed, irinotecan temozolomide, topotecan, radiation, and a combination of two or more thereof.

10. The method of claim 1, wherein the cancer has a deletion of a whole DACH1a gene.

11. The method of claim 10, wherein the cancer has a heterozygous deletion of the DACH1a gene.

12. The method of claim 10, wherein the cancer has a homozygous deletion of the DACH1a gene.

13. The method of claim 1, wherein the cancer has reduced expression of DACH1 protein as compared to the expression of DACH1 in non-cancer cells from the same organ or tissue as the cancer.

* * * * *